(12) United States Patent
Sakuma et al.

(10) Patent No.: US 7,265,137 B2
(45) Date of Patent: Sep. 4, 2007

(54) ACTIVATOR OF PEROXISOME PROLIFERATOR-ACTIVATED RE-CEPTOR δ

(75) Inventors: Shogo Sakuma, Saitama (JP); Tomio Yamakawa, Chiba (JP); Takashi Kanda, Chiba (JP); Seiichiro Masui, Saitama (JP)

(73) Assignee: Nippon Chemiphar Co., Ltd., Tokyo (JP)

( * ) Notice: Subject to any disclaimer, the term of this patent is extended or adjusted under 35 U.S.C. 154(b) by 412 days.

(21) Appl. No.: 10/486,783

(22) PCT Filed: Aug. 2, 2002

(86) PCT No.: PCT/JP02/07897

§ 371 (c)(1),
(2), (4) Date: Mar. 23, 2004

(87) PCT Pub. No.: WO03/016291

PCT Pub. Date: Feb. 27, 2003

(65) Prior Publication Data

US 2005/0054674 A1  Mar. 10, 2005

(30) Foreign Application Priority Data

Aug. 10, 2001  (JP) .............................. 2001-243734

(51) Int. Cl.
*A61K 31/421* (2006.01)
*A61K 31/426* (2006.01)
*C07D 213/30* (2006.01)
*C07D 277/20* (2006.01)

(52) U.S. Cl. ............. 514/365; 548/146; 548/203; 548/204; 548/236; 514/374

(58) Field of Classification Search ............ 548/146, 548/202, 203, 204, 215, 235, 236; 514/365, 514/374
See application file for complete search history.

(56) References Cited

U.S. PATENT DOCUMENTS 6,787,552 B2 * 9/2004 Sakuma et al. ............. 514/256
7,078,422 B2 * 7/2006 Sakuma et al. ............. 514/374

FOREIGN PATENT DOCUMENTS

| EP | 558062 | 9/1993 |
|---|---|---|
| EP | 1310494 | 5/2003 |
| WO | WO92/10468 | 6/1992 |
| WO | WO97/28115 | 8/1997 |
| WO | WO 01/00603 | 1/2001 |
| WO | WO 01/16120 | 3/2001 |
| WO | WO 01/40207 | 6/2001 |
| WO | WO 02/50048 | 6/2002 |
| WO | WO 02/092590 | 11/2002 |

OTHER PUBLICATIONS

Berger, J. et al., 1999, *J Biol Chem* 274:6718-6725.
Bright, S. et al., 1997, *J Immunol Methods* 207(1):23-31.
He, T.-C. et al., 1999, *Cell* 99:335-345.
Isseman, I. et al., 1990, *Nature* 347:645-650.
Kliewer, S. et al., 1992, *Nature* 358:771-774.
Kliewer, S. et al., 1994, *Proc Natl Acad Sci USA* 91:7335-7359.
Lehmann, J. et al., 1997, *J Biol Chem* 272(6):3406-3410.
Mano H., et al., 2000, *J Biol Chem* 175:8126-8132.
Oliver, W. et al., 2001, *Proc Natl Acad Sci USA* 98(9):5306-5311.

* cited by examiner

Primary Examiner—Golam M. M. Shameem
(74) Attorney, Agent, or Firm—Jones Day

(57) ABSTRACT

A compound represented by the following general formula (I):

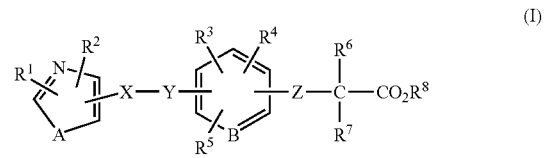

(wherein $R^1$ represents phenyl, etc. which can have substituents selected from the group consisting of $C_{1-8}$ alkyl, $C_{1-8}$ alkyl having halogen, halogen, hydroxyl, etc.; $R^2$ represents $C_{1-8}$ alkyl, etc.; A represents oxygen, sulfur, etc.; X represents $C_{1-8}$ alkylene chain, etc.; Y represents C(=O), CH=CH, etc.; $R^3$, $R^4$, and $R^5$ each represents hydrogen, $C_{1-8}$ alkyl, etc.; B represents CH or nitrogen; Z represents oxygen or sulfur; $R^6$ and $R^7$ each represents hydrogen, $C_{1-8}$ alkyl, etc.; and $R^8$ represents hydrogen or $C_{1-8}$ alkyl; provided that at least one of $R^3$, $R^4$, and $R^5$ is not hydrogen) or a salt of the compound; and a PPAR-δ activator which contains the compound or salt as the active ingredient.

5 Claims, No Drawings

ACTIVATOR OF PEROXISOME PROLIFERATOR-ACTIVATED RE-CEPTOR δ

TECHNICAL FIELD

The present invention relates to an activator of peroxisome proliferator activated receptor δ.

PRIOR ART

The peroxisome is a small organ present in cells of animals and plants, and its matrix contains various enzymes such as catalases. Various compounds such as fibrates, herbicides, and phthalic acid plasticizers are known as peroxisome proliferators which induce proliferation of peroxisomes.

Isseman, et al. have identified a nuclear receptor which is activated by peroxisome proliferator and called it peroxisome proliferator activated receptor (PPAR).—Nature, 347, p 645-650, 1990.

Three subtypes such as PPARα, PPARγ and PPARδ have been identified.—Proc. Natl. Acad. Sci. USA, 91, p 7335-7359, 1994.

The above-mentioned fibrates used as the serum triglyceride (TG) lowering drug can modulates PPARδ activity. Further, thiazolidine compounds (Troglitazone, Rosiglitazone, Pioglitazone) useful in the treatment of diabetes are also known as ligands of PPARγ.

It is reported that several compounds such as GW-2433 (Glaxo Wellcome), L-165041 (Merck), and YM-16638 (Yamanouchi Pharmaceutical) activate PPARδ. Each formula is as follows:

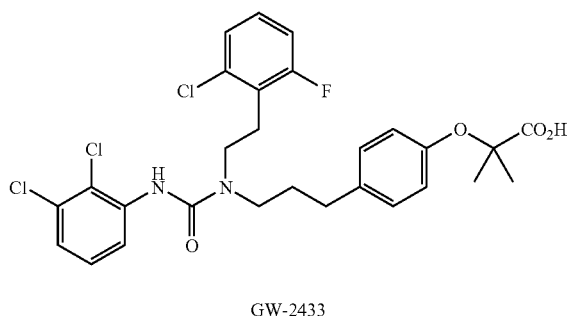

GW-2433

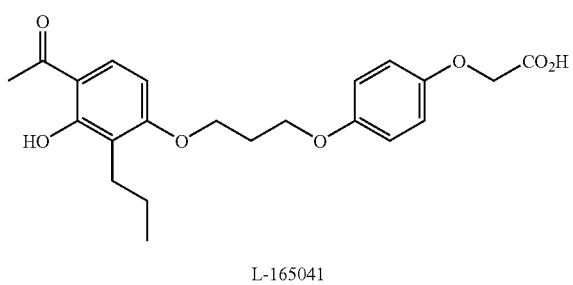

L-165041

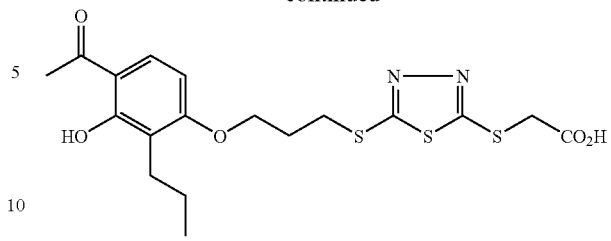

YM-16638

WO 92/10468 describes that GW-2433 can be employable for prevention and treatment of atherosclerosis.

WO 97/28115 describes that L-165041 can be employable for treatment of diabetes and suppression of obesity.

WO 99/04815 describes that YM-16638 shows effects for reducing serum cholesterol and reducing LDL cholesterol.

Recently, JBC, 272(6), p 3406-3410, 1997 and Cell, 99, p 335-345, 1999 describe proposal for application of PPAR δ ligand as an anti-cancer agent and an anti-inflammatory agent.

European Patent 558 062 describes the following compound A which has a structure similar to that of the general formula (I) [mentioned below] representing a compound of the invention:

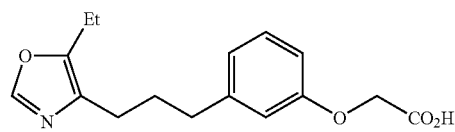

J. Immunol. Methods, 207(1), 23-31, 1997 describes a compound B having the following formula:

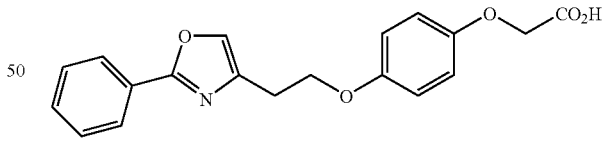

All of the compounds identified by the compound A, compound B and the general formula (I) of the invention may be described as compounds of phenoxyacetic acid type. However, there are clear structural differences between the compounds A, B and the compound of the invention. For example, the phenoxy group of the compounds A, B has the propyl group substituted with the oxazolyl group or the ethoxy group substituted with the oxazolyl group, while the compound of the invention has the propionyl group substituted with the oxazolyl group or the like. Further, the oxazole ring of the compounds A, B has only one of the ethyl group or the phenyl group, while the compound of the invention may have both of the groups.

In addition, while the above-mentioned EP 558 062 teaches that the compound A is of value for treatment of hyperthrombinemia and as blood pressure depressant, no mention is given with respect to an effect as PPARδ ligand.

Further, while the J. Immunol. Methods teaches the use of the compound B as blood pressure depressant, there is no concrete description to teach that the compound is effective as PPARδ ligand.

Recently, WO 01/40207 describes a substituted oxa(thia)zole derivative showing an agonist action for PPARα, and WO 01/16120 describes an oxa(thia)zole derivative substituted with a biaryl group which is employable as a PPAR controlling agent.

In comparison with the compounds of the invention, the compound of WO 01/40207 has C(=O)NH as X and an alkylene chain bond as Y, and the compound of WO 01/16120 has an alkylene chain as X and O, X or the like as Y. Accordingly, the structural difference is clear.

Proc. Natl. Acad. Sci. U.S.A. 2001, Apr. 24; 98(9): 5306-11, and WO01/00603 describe that the following compound GW-501516 has a highly selective agonist action for PPARα.

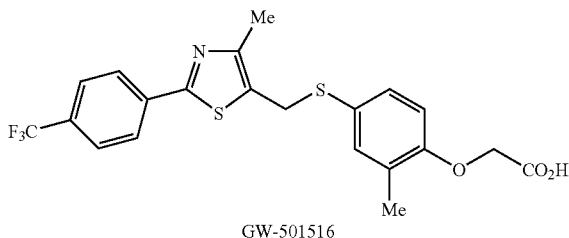

GW-501516

There is a clear structural difference between the GW-501516 and the compound of the invention, that is, GW-501516 has the methyl group as X of the present invention, and S as Y.

Further, each of WO 02/14291 (Nippon Chemiphar Co., Ltd.) and WO 02/50048 (GLAXO) discloses a compound having an agonist action of peroxisome proliferator activated receptor. WO 02/50048 describes synthetic intermediates such as ethyl[2-methyl-4-(3-(4-methyl-2-[4-(trifluoromethyl)phenyl]-1,3-thiazol-5-yl)propanoyl)phenoxy] acetic acid, ethyl[2-methyl-4-((4-methyl-2-[4-(trifluoromethyl)phenyl]-1,3-thiazol-5-yl)acetyl)phenoxy] acetic acid, ethyl[4-(1-hydroxy-3-(4-methyl-2-[4-(trifluoromethyl)phenyl]-1,3-thiazol-5-yl)propyl)-2-methylphenoxy]acetic acid, ethyl[4-(1-hydroxy-2-(4-methyl-2-[4-(trifluoromethyl)phenyl]-1,3-thiazol-5-yl)ethyl)-2-methylphenoxy]acetic acid.

The present invention provides a compound having the below-mentioned general formula (I) and a salt thereof, which has an agonist action (action as activator of peroxisome proliferator activated receptor δ.

DISCLOSURE OF INVENTION

The invention resides in a compound having the following general formula (I) or a salt thereof:

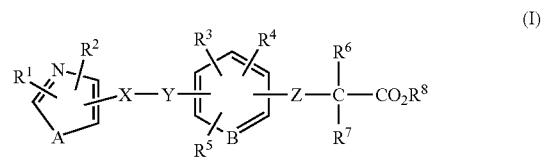

(wherein $R^1$ is phenyl, naphthyl, pyridyl, thienyl, furyl, quinolyl or benzothienyl, any of which can have substituents selected from the group consisting of $C_{1-8}$ alkyl, $C_{1-8}$ alkyl having halogen, $C_{1-8}$ alkoxy, $C_{1-8}$ alkoxy having halogen, $C_{2-8}$ alkenyl, $C_{2-8}$ alkynyl, halogen, $C_{2-7}$ acyl, benzoyl, hydroxyl, nitro, amino, phenyl and pyridyl;

$R^2$ is $C_{1-8}$ alkyl, $C_{1-8}$ alkyl having halogen, $C_{2-8}$ alkenyl, $C_{2-8}$ alkynyl, 3-7 membered cycloalkyl, $C_{1-8}$ alkyl having 3-7 membered cycloalkyl, or $C_{1-6}$ alkyl substituted with phenyl, naphthyl or pyridyl, any of which can have substituents selected from the group consisting of $C_{1-8}$ alkyl, $C_{1-8}$ alkyl having halogen, $C_{1-8}$ alkoxy, $C_{1-8}$ alkoxy having halogen, $C_{2-8}$ alkenyl, $C_{2-8}$ alkynyl, halogen, $C_{2-7}$ acyl, benzoyl, hydroxyl, nitro, amino, phenyl and pyridyl;

A is oxygen, sulfur or $NR^9$ in which $R^9$ is hydrogen or $C_{1-8}$ alkyl;

X is a $C_{1-8}$ alkylene chain which can have substituents selected from the group consisting of $C_{1-8}$ alkyl, $C_{1-8}$ alkoxy and hydroxyl and which can contain a double bond;

Y is C(=O), C(=N—OR$^{10}$), CH(OR$^{11}$), CH=CH, C≡C, or C(=CH$_2$) in which each of $R^{10}$ and $R^{11}$ is hydrogen or $C_{1-8}$ alkyl;

each of $R^3$, $R^4$ and $R^5$ is hydrogen, $C_{1-8}$ alkyl, $C_{1-8}$ alkyl having halogen, $C_{1-8}$ alkoxy, $C_{1-8}$ alkoxy having halogen, $C_{2-8}$ alkenyl, $C_{2-8}$ alkynyl, halogen, $C_{2-7}$ acyl, benzoyl, hydroxyl, nitro, amino, phenyl, or pyridyl;

B is CH or nitrogen;

Z is oxygen or sulfur;

each of $R^6$ and $R^7$ is hydrogen, $C_{1-8}$ alkyl, $C_{1-8}$ alkyl having halogen; and $R^8$ is hydrogen or $C_{1-8}$ alkyl;

provided that at least one of $R^3$, $R^4$ and $R^5$ is not hydrogen.

The invention also provides an activator of peroxisome proliferator activated receptor δ, which contains as an effective component a compound of the formula (I) or a salt thereof.

DETAILED DESCRIPTION OF THE INVENTION

In the formula (I), examples of the alkyl groups having 1-8 carbon atoms include methyl, ethyl, propyl, isopropyl, butyl, isobutyl, t-butyl and pentyl.

Examples of the alkyl groups having 1-8 carbon atoms and a halogen substituent include methyl, ethyl, propyl, isopropyl, butyl, and t-butyl which are substituted with 1-3 halogens such as fluorine, chlorine, and bromine. Preferred are trifluoromethyl, chloromethyl, 2-chloroethyl, 2-bromoethyl and 2-fluoroethyl.

Examples of the alkoxy groups having 1-8 carbon atoms include methoxy, ethoxy, propoxy, isopropoxy, butoxy, isobutoxy, t-butoxy and pentyloxy.

Examples of the alkoxy groups having 1-8 carbon atoms and a halogen substituent include methoxy, ethoxy, propoxy, isopropoxy, butoxy and t-butoxy groups substituted with 1-3 halogen atoms such as fluorine atom, chlorine atom or bromine atom. Trifluoromethoxy, chloromethoxy, 2-chloroethoxy, 2-bromoethoxy and 2-fluoroethoxy are preferred.

Examples of the alkenyl groups having 2-8 carbon atoms include vinyl and allyl.

Examples of the alkynyl groups having 2-8 carbon atoms include propargyl.

Examples of the 3-7 membered cycloalkyl groups include cyclohexyl and cyclopentyl.

Examples of the alkyl groups having 1-8 carbon atoms and a 3-7 membered cycloalkyl substituent include cyclohexylmethyl and cyclopentylmethyl.

(1) A preferred compound of the invention is a compound of the formula (I) or salt thereof, in which $R^1$ is phenyl which can have substituents selected from the group consisting of $C_{1-8}$ alkyl, $C_{1-8}$ alkyl having 1-3 halogen atoms, $C_{1-8}$ alkoxy, $C_{1-8}$ alkoxy having 1-3 halogen atoms, $C_{2-8}$ alkenyl, $C_{2-8}$ alkynyl, halogen, $C_{2-7}$ acyl, benzoyl, hydroxyl, nitro, amino, phenyl and pyridyl.

(2) Another preferred compound of the invention is a compound of the formula (I), a salt thereof or (1), in which $R^2$ is $C_{2-8}$ alkyl.

(3) A further preferred compound of the invention is a compound of the formula (I), a salt thereof, (1) or (2), in which $R^1$ is attached to the 2nd position. In the case that $R^1$ is attached to the 2nd position, $R^4$ is attached to the 4th position and —X—Y— is attached to the 5th position, or $R^4$ is attached to the 5th position and —X—Y— is attached to the 4th position.

(4) A furthermore preferred compound of the invention is a compound of the formula (I), a salt thereof, (1), (2) or (3), in which A is oxygen or sulfur.

(5) A still further preferred compound of the invention is a compound of the formula (I), a salt thereof, (1), (2), (3) or (4), in which X is a $C_{1-8}$ alkylene chain.

(6) A still further preferred compound of the invention is a compound of the formula (I), a salt thereof, (1), (2), (3), (4) or (5), in which Y is C(=O).

(7) A still further preferred compound of the invention is a compound of the formula (I), a salt thereof, (1), (2), (3), (4), (5) or (6), in which each of $R^3$, $R^4$ and $R^5$ is hydrogen, $C_{1-8}$ alkyl or $C_{1-8}$ alkyl having halogen.

(8) A still further preferred compound of the invention is a compound of the formula (I), a salt thereof, (1), (2), (3), (4), (5), (6) or (7), in which B is CH.

(9) A still further preferred compound of the invention is a compound of the formula (I), a salt thereof, (1), (2), (3), (4), (5), (6), (7) or (8), in which Z is oxygen.

(10) A still further preferred compound of the invention is a compound of the formula (I), a salt thereof, (1), (2), (3), (4), (5), (6), (7), (8) or (9), in which each of $R^6$ and $R^7$ is hydrogen or $C_{1-4}$ alkyl.

(11) A still further preferred compound of the invention is a compound of the formula (I), a salt thereof, (1), (2), (3), (4), (5), (6), (7), (8) or (9), in which $R^8$ is hydrogen.

(12) A still further preferred compound of the invention is a compound of the formula (I) or a salt thereof, in which $R^1$ is phenyl or naphthyl, each of which can have substituents selected from the group consisting of $C_{1-8}$ alkyl, $C_{1-8}$ alkyl having halogen, $C_{1-8}$ alkoxy, $C_{1-8}$ alkoxy having halogen, $C_{2-8}$ alkenyl, $C_{2-8}$ alkynyl, halogen, $C_{2-7}$ acyl, benzoyl, hydroxyl, nitro, amino, phenyl and pyridyl;

$R^2$ is $C_{2-8}$ alkyl;

A is oxygen or sulfur;

X is a $C_{1-8}$ alkylene chain which can have a $C_{1-8}$ alkyl substituent and which can contain a double bond;

Y is C(=O), CH=CH, or C(=$CH_2$);

each of $R^3$, $R^4$ and $R^5$ is hydrogen, $C_{1-8}$ alkyl, $C_{1-8}$ alkyl having halogen, $C_{1-8}$ alkoxy, $C_{1-8}$ alkoxy having halogen, $C_{2-8}$ alkenyl, $C_{2-8}$ alkynyl, halogen, $C_{2-7}$ acyl, benzoyl, hydroxyl, nitro, amino, phenyl, or pyridyl;

B is CH;

Z is oxygen or sulfur;

each of $R^6$ and $R^7$ is hydrogen or $C_{1-8}$ alkyl; and $R^8$ is hydrogen or $C_{1-8}$ alkyl.

(13) A still further preferred compound of the invention is a compound of (12), in which X is a $C_{1-8}$ alkylene chain.

(14) A still further preferred compound of the invention is a compound of (12) or (13), in which $R^1$ is attached to the 2nd position.

(15) A still further preferred compound of the invention is a compound of (12), (13) or (14), in which $R^8$ is hydrogen.

(16) A still further preferred compound of the invention is a compound of (12), (13), (14) or (15), in which the substituents of $R^3$, $R^4$ and $R^5$ other than hydrogens are placed at ortho-positions with respect to -Z-$CR^6R^7CO_2R^8$.

The compound of the formula (I) can be present in the form of geometrical isomers such as cis and trans and optical isomers. These isomers are included in the compounds of the invention.

Further, the compounds of the invention can be in the form of pharmaceutically acceptable salts such as alkali metal salts, e.g., sodium salt and potassium salt.

The processes for preparing the compound of the formula (I) according to the invention are described below.

[Synthetic process 1]

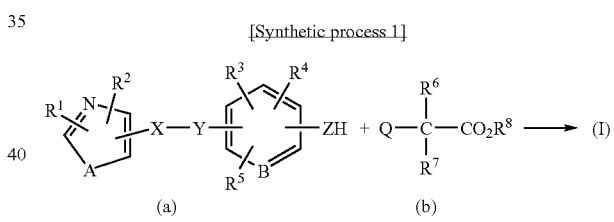

(a)                                  (b)

[in the formulas, Q is a releasing group such as tosyloxy or halogen (e.g., bromine), and $R^1$, $R^2$, $R^3$, $R^4$, $R^5$, $R^6$, $R^7$, $R^8$, A, X, Y, B and Z are those described hereinbefore.

In the above-described process, the compound of the formula (I) according to the invention can be prepared by reacting a phenol or thiophenol compound of the general formula (a) with an acetic acid derivative of the general formula (b). The reaction can be carried out in a solvent such as methyl ethyl ketone in the presence of a base such as potassium carbonate.

The starting compound of the formula (a), can be prepared by a process similar to the below-mentioned synthetic scheme.

[Synthesis example 1 for starting compound in which Y is CO, Z is O]

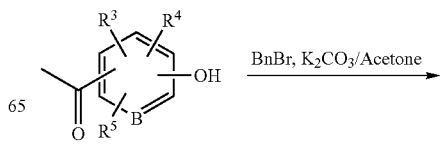

-continued

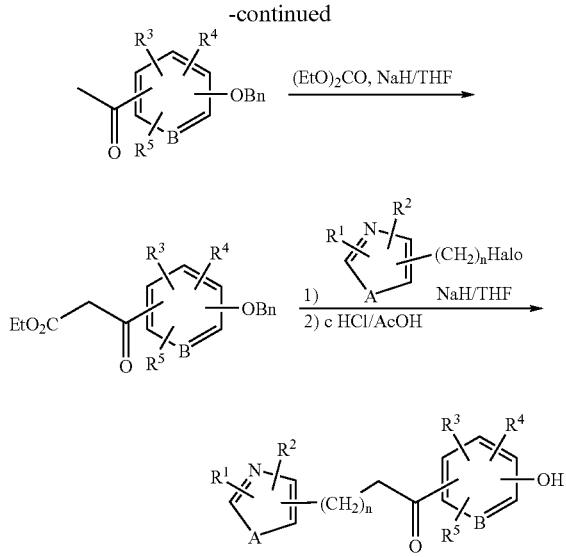

[in the formulas, n is an integer of 1 to 7, Bn is benzyl, and $R^1$, $R^2$, $R^3$, $R^4$, $R^5$, A and B are those described hereinbefore.]

[Synthesis example 2 for starting compound in which Z is S]

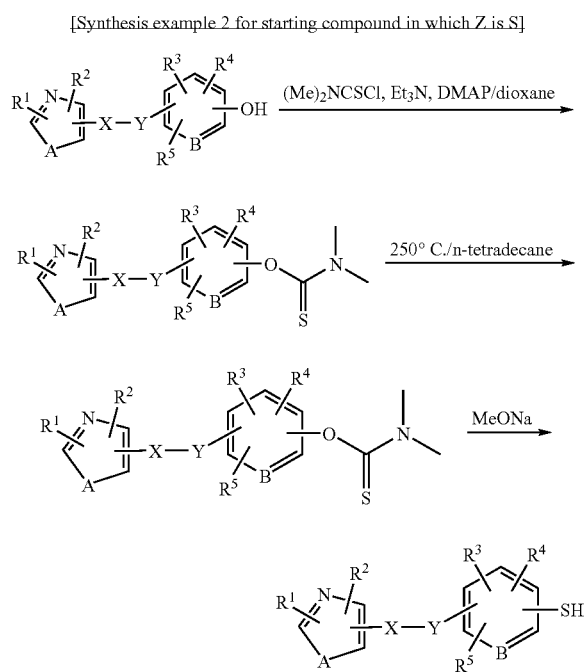

[in the formulas, $R^1$, $R^2$, $R^3$, $R^4$, $R^5$, A, B, X and Y are those described hereinbefore.]

The phenol compound is treated with dimethylthiocarbamoyl chloride in the presence of a base such as triethylamine to obtain a dimethylthiocarbamoyloxy compound. The dimethylthiocarbamoyloxy compound is heated in n-tetradecane or no solvent to obtain a dimethylcarbamoylsulfanyl compound as a rearranged compound. The dimethylcarbamoyl group is treated with NaOH or MeONa to be converted to a thiophenol compound.

[Synthesis example 3 for starting compound in which Y is CO, Z is O]

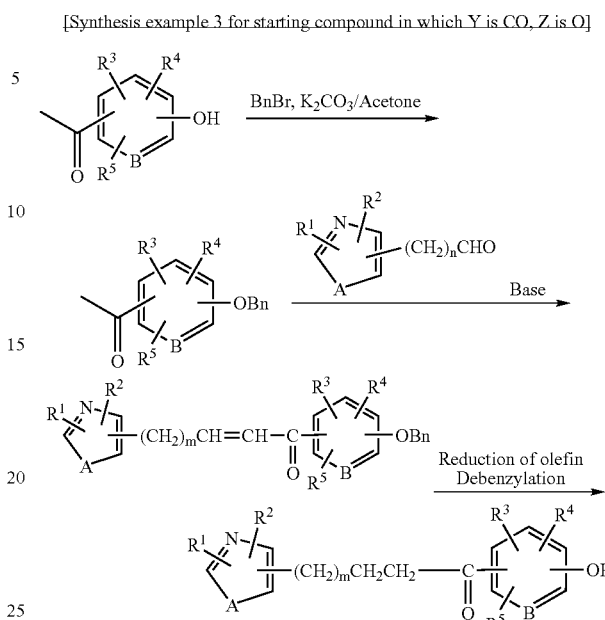

[in the formulas, m is an integer of 0 to 6, and $R^1$, $R^2$, $R^3$, $R^4$, $R^5$, A, B and Bn are those described hereinbefore.]

The acetophenone compound and the aldehyde compound synthesized according to a conventional method are condensed with hydration using a base such as NaOH, KOH, MeONa, EtONa, piperidine in a solvent such as methanol, ethanol, anhydrous benzene to obtain a α,β-unsaturated ketone compound. The α,β-unsaturated ketone compound is treated, for example subjected to a hydride contact reduction to conduct reduction of the olefin and the debenzylation to obtain the subject compound.

[Synthesis example 4 for starting compound in which Y is CO, Z is O]

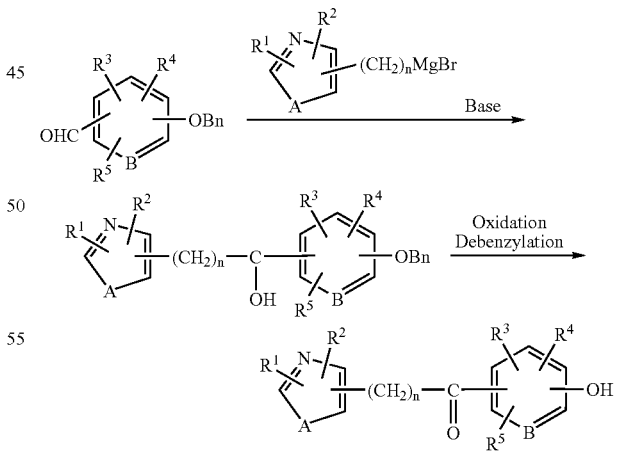

[in the formulas, $R^1$, $R^2$, $R^3$, $R^4$, $R^5$, A, B, n and Bn are those described hereinbefore.]

The benzaldehyde compound is treated with a Grignard reagent obtained according to a conventional method in the presence of a solvent such as a ether or THF under the condition of a low temperature to obtain an alcohol compound. The alcohol compound can be converted into a ketone compound by using a Jones reagent (chromium(VI) oxide-sulfuric acid-acetone) or chromium(VI)-pyridine complex (e.g., pyridinium chlorochromate, pyridinium dichromate). The alcohol compound can also be converted into the ketone body in the same manner by using DMSO oxidation. Finally, the ketone body is subjected to debenzylation to be converted into the subject phenol compound.

[Synthesis example 5 for starting compound in which Z is O]

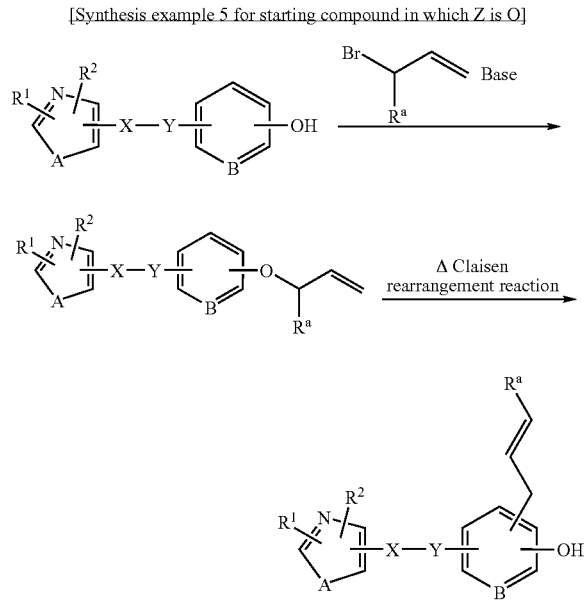

[in the formulas, $R^a$ is hydrogen atom or an alkyl group having 1 to 5 carbon atoms, and $R^1$, $R^2$, A, X, Y and B are those described hereinbefore.]

The phenol compound is subjected to an allylation according to a conventional method, and heated (at 150° C. or higher) with no solvent or in a solvent such as quinoline to obtain a compound having the rearranged allyl group at the ortho-position.

[Synthesis example 6 for starting compound in which Z is O]

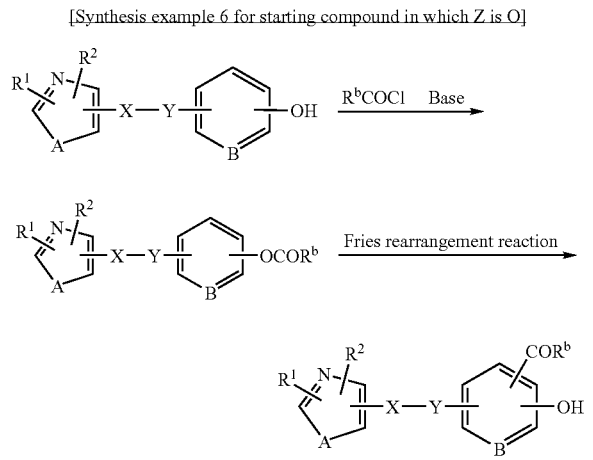

[in the formulas, $R^b$ is an alkyl group having 1 to 6 carbon atoms, and $R^1$, $R^2$, A, X, Y and B are those described hereinbefore.]

The phenol compound is subjected to an acylation according to a conventional method, and heated in the presence of a Lewis acid catalyst to obtain a compound having the rearranged acyl group at the ortho-position.

[Synthesis example 7 for starting compound in which Y is CH=CH]

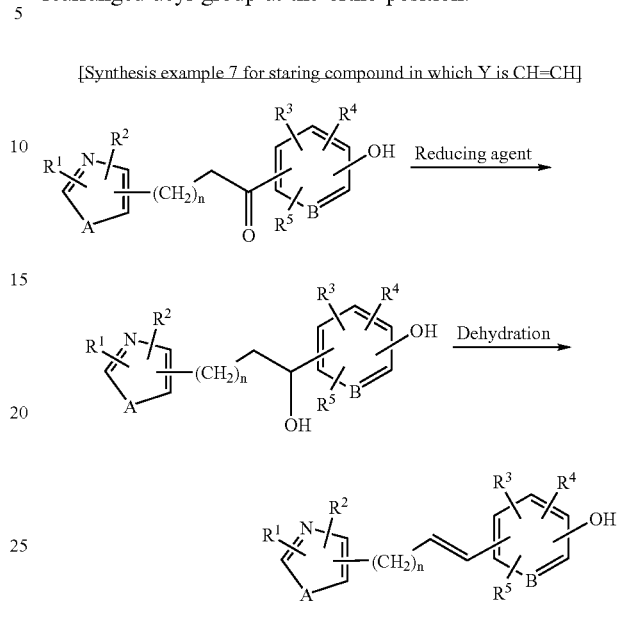

[in the formulas, $R^1$, $R^2$, $R^3$, $R^4$, $R^5$, A, B, n and Bn are those described hereinbefore.]

The phenol compound obtained in the Synthesis example 1 for starting compound is treated with a reducing agent such as lithium aluminum hydride, sodium boron hydride to obtain an alcohol compound. The alcohol compound is subjected to dehydration using a halogenation agent, a sulfonation agent or a dehydration agent to obtain an olefin compound.

[Synthesis process 2 (wherein $R^8$ is H)]

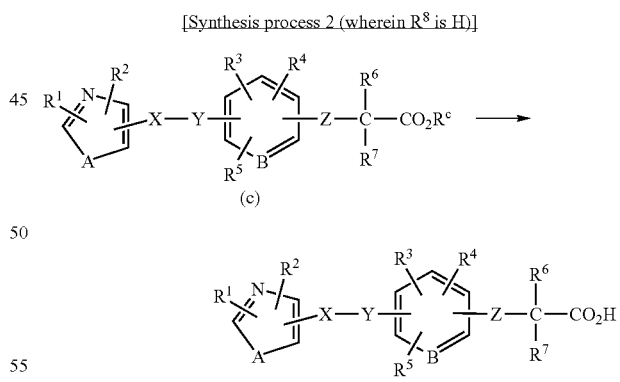

[in the formulas, $R^c$ is an alkyl group having 1 to 8 carbon atoms, and $R^1$, $R^2$, $R^3$, $R^4$, $R^5$, $R^6$, $R^7$, A, X, Y, B and Z are those described hereinbefore.]

In the above-illustrated process for preparation, a compound of the formula (I) ($R^8$=H) according to the invention can be obtained by the ester compound of the formula (c) is hydrolyzed in a solvent such as aqueous ethanol in the presence of a base such as sodium hydroxide, potassium hydroxide or lithium hydroxide.

[Synthesis process 3 (wherein Y is C(=N—OH))]

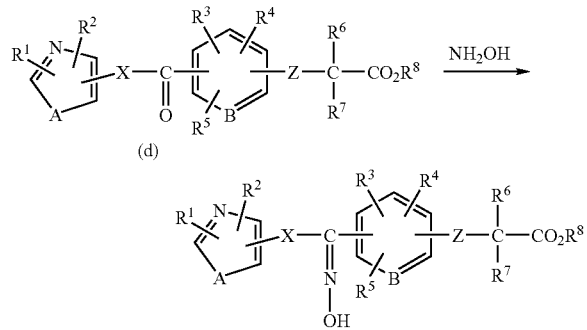

(d)

[in the formulas, $R^1$, $R^2$, $R^3$, $R^4$, $R^5$, $R^6$, $R^7$, A, X, B and Z are those described hereinbefore].

In the above-illustrated process, a compound of the formula (I) ($Y$ is $C(=N-OH)$) according to the invention can be obtained by reacting the ketone compound of the formula (d) with hydroxylamine.

[Synthetic process 4 (wherein Y is C(=CH_2))]

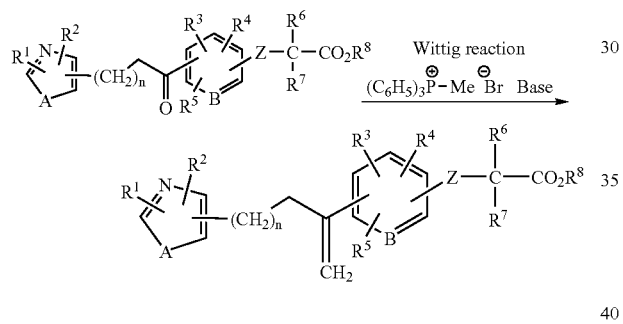

[in the formulas, $R^1$, $R^2$, $R^3$, $R^4$, $R^5$, $R^6$, $R^7$, A, B, Z and n are those described hereinbefore].

The ketone compound (Y is C(=O)) can be treated with methyl triphenyl phosphonium bromide in the presence of a base such as t-BuOK, n-BuLi, sec-BuLi, EtONa in a solvent such as a dry ether or THF (according to Wittig reaction) to introduce a methylene chain into the compound.

[Synthetic process 5 (wherein Y is C(=CH_2))]

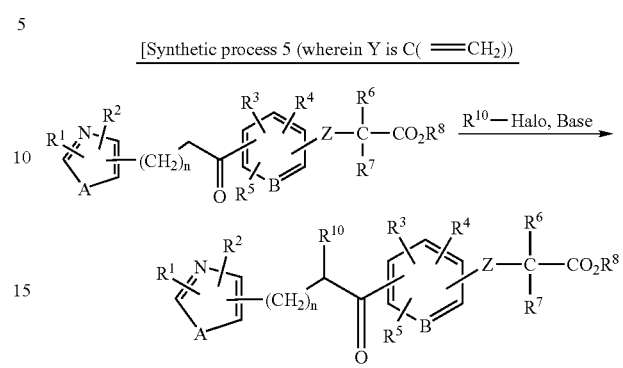

[in the formulas, $R^{10}$ is an alkyl group having 1 to 10 carbon atoms, $R^1$, $R^2$, $R^3$, $R^4$, $R^5$, $R^6$, $R^7$, $R^8$, A, B, Z and n are those described hereinbefore].

The ketone compound (Y is C(=O)) can be treated with alkyl halide such as iodomethane in the presence of a base such as t-BuOK, BuLi, EtONa, NaH in a solvent such as a dry ether or THF to introduce an alkyl chain into the compound at the α-position of the carbonyl group.

The representative compounds of the invention are described below.

(1) Compounds of the Following Formula

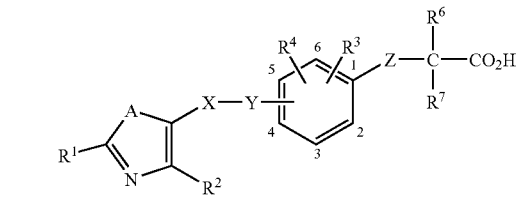

Compounds of the formula (I) in which $R^5$ is H, B is CH, $R^8$ is H, and $R^1$, $R^2$, $R^3$, $R^4$, $R^6$, $R^7$, A, X, Y and Z are shown in Tables 1 to 4.

TABLE 1

| A | $R^1$ | $R^2$ | $R^3$ | $R^4$ | $R^6$ | $R^7$ | X | Y | Z |
|---|---|---|---|---|---|---|---|---|---|
| S | (4-CF$_3$)Ph | Isopropyl | Me(2) | H | H | H | CH$_2$CH$_2$ | C=O(4) | O |
| S | (4-CF$_3$)Ph | Isopropyl | Me(2) | H | Me | Me | CH$_2$CH$_2$ | C=O(4) | O |
| S | (4-CF$_3$)Ph | Isopropyl | Me(2) | H | H | H | CH$_2$ | CH=CH(4) | O |
| S | (4-CF$_3$)Ph | Hexyl | Me(2) | H | H | H | CH$_2$CH$_2$ | C=O(4) | O |
| S | (4-CF$_3$)Ph | Hexyl | Me(2) | H | Me | Me | CH$_2$CH$_2$ | C=O(4) | O |
| S | (4-CF$_3$)Ph | Isopropyl | Me(2) | H | Me | Me | CH$_2$ | CH=CH(4) | O |
| S | (4-CF$_3$)Ph | Isopropyl | Me(3) | H | H | H | CH$_2$CH$_2$ | C=O(4) | O |
| S | (4-CF$_3$)Ph | Isopropyl | Me(3) | H | Me | Me | CH$_2$CH$_2$ | C=O(4) | O |
| S | (4-CF$_3$)Ph | Isopropyl | Pr(2) | H | H | H | CH$_2$CH$_2$ | C=O(4) | O |
| S | (4-CF$_3$)Ph | Isopropyl | Allyl(2) | H | H | H | CH$_2$CH$_2$ | C=O(4) | O |
| S | (4-CF$_3$)Ph | Isopropyl | Me(2) | H | H | H | CH=CH | C=O(4) | O |
| S | (4-CF$_3$)Ph | Isopropyl | Me(2) | H | Me | Me | CH=CH | C=O(4) | O |
| S | (4-OMe)Ph | Isopropyl | Me(2) | H | H | H | CH$_2$CH$_2$ | C=O(4) | O |
| S | (3,5-F)Ph | Isopropyl | Me(2) | H | H | H | CH$_2$CH$_2$ | C=O(4) | O |
| S | (3,5-F)Ph | Isopropyl | Me(2) | H | Me | Me | CH$_2$CH$_2$ | C=O(4) | O |
| S | 2-Naphthyl | Isopropyl | Me(2) | H | H | H | CH$_2$CH$_2$ | C=O(4) | O |
| S | 2-Naphthyl | Isopropyl | Me(2) | H | Me | Me | CH$_2$CH$_2$ | C=O(4) | O |
| S | (4-Bu)Ph | Isopropyl | Me(2) | H | H | H | CH$_2$CH$_2$ | C=O(4) | O |
| S | (4-Bu)Ph | Isopropyl | Me(2) | H | Me | Me | CH$_2$CH$_2$ | C=O(4) | O |
| S | (4-CF$_3$)Ph | Isopropyl | Cl(2) | H | H | H | CH$_2$CH$_2$ | C=O(4) | O |

TABLE 1-continued

| A | R$^1$ | R$^2$ | R$^3$ | R$^4$ | R$^6$ | R$^7$ | X | Y | Z |
|---|---|---|---|---|---|---|---|---|---|
| S | (4-CF$_3$)Ph | Isopropyl | Cl(2) | H | Me | Me | CH$_2$CH$_2$ | C=O(4) | O |
| S | (4-CF$_3$)Ph | Isopropyl | Me(2) | H | H | H | CH$_2$CH$_2$ | C=O(5) | O |
| S | (4-CF$_3$)Ph | Isopropyl | Me(2) | H | Me | Me | CH$_2$CH$_2$ | C=O(5) | O |
| S | (4-CF$_3$)Ph | Isopropyl | Me(2) | H | Me | H | CH$_2$CH$_2$ | C=O(4) | O |

Remark:
Numeral in ( ) means a position of the group.

TABLE 2

| A | R$^1$ | R$^2$ | R$^3$ | R$^4$ | R$^6$ | R$^7$ | X | Y | Z |
|---|---|---|---|---|---|---|---|---|---|
| S | (4-CF$_3$)Ph | Hexyl | Me(2) | H | Me | Me | CH$_2$ | CH=CH(4) | O |
| S | (4-CF$_3$)Ph | Hexyl | Me(2) | H | Me | Me | CH$_2$ | CH$_2$CH$_2$(4) | O |
| S | (4-CF$_3$)Ph | Hexyl | Me(2) | H | Me | Me | CH$_2$CH$_2$ | C=O(5) | O |
| S | (4-CF$_3$)Ph | Ethyl | Me(2) | H | H | H | CH$_2$CH$_2$ | C=O(4) | O |
| S | (4-CF$_3$)Ph | Ethyl | Me(2) | H | Me | Me | CH$_2$CH$_2$ | C=O(4) | O |
| S | (4-Me)Ph | Isopropyl | Me(2) | H | H | H | CH$_2$CH$_2$ | C=O(4) | O |
| S | (4-Me)Ph | Isopropyl | Me(2) | H | Me | Me | CH$_2$CH$_2$ | C=O(4) | O |
| S | (4-CF$_3$)Ph | Isopropyl | Me(2) | H | H | H | CH$_2$CH$_2$ | C=O(4) | S |
| S | (4-Et)Ph | Isopropyl | Me(2) | H | H | H | CH$_2$CH$_2$ | C=O(4) | O |
| S | (4-iPr)Ph | Isopropyl | Me(2) | H | H | H | CH$_2$CH$_2$ | C=O(4) | O |
| S | (4-t-Bu)Ph | Isopropyl | Me(2) | H | H | H | CH$_2$CH$_2$ | C=O(4) | O |
| S | (4-Cl)Ph | Isopropyl | Me(2) | H | H | H | CH$_2$CH$_2$ | C=O(4) | O |
| S | (4-F)Ph | Isopropyl | Me(2) | H | H | H | CH$_2$CH$_2$ | C=O(4) | O |
| S | (4-NO$_2$)Ph | Isopropyl | Me(2) | H | H | H | CH$_2$CH$_2$ | C=O(4) | O |
| S | (4-NMe$_2$)Ph | Isopropyl | Me(2) | H | H | H | CH$_2$CH$_2$ | C=O(4) | O |
| S | (4-CF$_3$)Ph | Isopropyl | Me(2) | H | Me | Me | CH$_2$CH$_2$ | C=O(4) | S |
| S | (4-Et)Ph | Isopropyl | Me(2) | H | Me | Me | CH$_2$CH$_2$ | C=O(4) | O |
| S | (4-iPr)Ph | Isopropyl | Me(2) | H | Me | Me | CH$_2$CH$_2$ | C=O(4) | O |
| S | (4-t-Bu)Ph | Isopropyl | Me(2) | H | Me | Me | CH$_2$CH$_2$ | C=O(4) | O |
| S | (4-Cl)Ph | Isopropyl | Me(2) | H | Me | Me | CH$_2$CH$_2$ | C=O(4) | O |
| S | (4-F)Ph | Isopropyl | Me(2) | H | Me | Me | CH$_2$CH$_2$ | C=O(4) | O |
| S | (4-NO$_2$)Ph | Isopropyl | Me(2) | H | Me | Me | CH$_2$CH$_2$ | C=O(4) | O |
| S | (4-NMe$_2$)Ph | Isopropyl | Me(2) | H | Me | Me | CH$_2$CH$_2$ | C=O(4) | O |
| S | (4-Cl)Ph | Isopropyl | Allyl(2) | H | H | H | CH$_2$CH$_2$ | C=O(4) | O |

Remark:
Numeral in ( ) means a position of the group.

TABLE 3

| A | R$^1$ | R$^2$ | R$^3$ | R$^4$ | R$^6$ | R$^7$ | X | Y | Z |
|---|---|---|---|---|---|---|---|---|---|
| O | (2-OH,4-Cl)Ph | Isopropyl | Allyl(2) | H | H | H | CH$_2$CH$_2$ | C=O(4) | O |
| O | (2-OH,4-Cl)Ph | Isopropyl | Me(2) | H | Me | Me | CH$_2$CH$_2$ | CH=CH(3) | O |
| O | (4-Me)Ph | Isopropyl | Me(2) | H | H | H | CH$_2$CH$_2$ | C=O(4) | S |
| O | (2,4-Me)Ph | Isopropyl | Pr(2) | H | Me | Me | CH(Me)CH$_2$ | C=O(4) | O |
| S | (2-OH,4-Me)Ph | Bu | Benzyl(2) | H | H | H | CH$_2$CH$_2$ | C=O(3) | O |
| NH | (2-OH,4-CF$_3$)Ph | Pr | Acetyl(2) | H | H | H | CH$_2$CH$_2$ | C=O(4) | O |
| N—Me | (2-OH,4-Cl)Ph | Hexyl | Cl(2) | H | H | H | CH$_2$CH$_2$ | C=O(4) | O |
| S | (2,4-Me)Ph | Et | Br(2) | H | H | H | CH$_2$CH$_2$ | C=O(4) | S |
| S | (3,4-Cl)Ph | Bu | CF$_3$(2) | H | Me | Et | CH$_2$CH$_2$ | C=O(4) | O |
| S | (2,4-Me)Ph | Hexyl | Me(2) | Me(6) | Me | Me | CH(Me)CH$_2$ | C=O(4) | O |
| S | (2,4-Cl)Ph | Bu | Me(2) | Me(3) | H | H | CH$_2$CH$_2$ | C=O(4) | O |
| S | (2-OH,3,4-Me)Ph | Pr | Cl(2) | Cl(6) | H | H | CH$_2$CH$_2$ | CH=CH(4) | O |
| S | (2,4-F)Ph | Hexyl | Me(2) | H | Me | Me | CH$_2$CH$_2$ | CH=CH(4) | O |
| O | (3,4,5-Me)Ph | Et | Me(2) | H | H | H | CH$_2$CH$_2$ | C=O(4) | S |
| O | (2-OH,3,4-Me)Ph | Bu | Me(3) | H | Me | Me | CH$_2$CH$_2$ | C=O(4) | O |
| O | (2-OH,4-CF$_3$)Ph | Phenylethyl | Me(2,6) | H | H | H | CH$_2$CH$_2$ | C=O(3) | O |
| O | (4-OMe)Ph | Isopropyl | Me(2) | Me(6) | H | H | CH$_2$CH$_2$ | C=O(4) | O |
| S | (2-Cl,4-OPh)Ph | Isopropyl | Acetyl(2) | H | H | H | CH$_2$CH$_2$ | C=O(4) | O |
| NH | 1-Naphthyl | Isopropyl | Cl(3) | H | H | H | CH$_2$ | CH=CH(4) | S |
| N—Me | 2-Naphthyl | Isopropyl | Br(3) | H | Me | Et | CH(Me)CH$_2$ | C=O(4) | O |
| S | 2-Quinolyl | Isopropyl | CF$_3$(2) | H | Me | Me | CH$_2$CH$_2$ | C=O(4) | O |
| NH | 8-Quinolyl | Isopropyl | Me(2) | H | Me | Me | CH$_2$CH$_2$ | C=O(4) | O |
| N—Me | 3-Quinolyl | Isopropyl | Me(2) | H | H | H | CH$_2$CH$_2$ | C=O(4) | O |
| S | 2-Pyrimidyl | Isopropyl | Allyl(3) | H | H | H | CH$_2$CH$_2$ | C=O(4) | O |

Remark:
Numeral in ( ) means a position of the group.

TABLE 4

| A | R¹ | R² | R³ | R⁴ | R⁶ | R⁷ | X | Y | Z |
|---|---|---|---|---|---|---|---|---|---|
| S | 2-Thyenyl | Isopropyl | Me(2) | H | H | H | $CH_2$ | CH=CH(4) | S |
| S | 2-Pyridyl | Isopropyl | Me(2) | H | H | H | $CH_2CH_2$ | C=O(4) | O |
| S | 4-Pyridyl | Isopropyl | Me(2) | H | H | H | $CH_2CH_2$ | C=O(4) | O |
| S | 5-Et-2-Pyridyl | Isopropyl | Me(2) | H | H | H | $CH_2CH_2$ | C=O(4) | O |
| S | 5-Me-2-Pyridyl | Isopropyl | Me(2) | H | H | H | $CH_2CH_2$ | C=O(4) | O |
| S | 5-Et-2-Pyridyl | Isopropyl | Me(2) | H | Me | Me | $CH_2CH_2$ | C=O(4) | O |
| S | 2-Furanyl | Isopropyl | Me(2) | H | H | H | $CH_2CH_2$ | C=O(4) | O |
| S | 2-Imidazolyl | Isopropyl | Me(2) | H | Me | Et | $CH_2CH_2$ | C=O(4) | O |
| O | 2-Indolyl | Isopropyl | Pr(2) | H | Me | Me | $CH_2CH_2$ | C=O(4) | O |
| O | 2-Benzofuranyl | Benzyl | Benzyl(2) | H | Me | Me | $CH_2CH_2$ | C=O(4) | O |
| O | 2-Benzothienyl | Isopropyl | Acetyl(2) | H | Me | Me | $CH_2CH_2$ | C=O(4) | S |
| O | 2-Benzoimidazolyl | Isopropyl | Cl(2) | Cl(6) | Me | Me | $CH_2CH_2$ | C=O(4) | S |
| S | (4-$CF_3$)Ph | sec-Bu | Me(2) | H | H | H | $CH_2CH_2$ | C=O(4) | O |
| S | (4-$CF_3$)Ph | sec-Bu | Me(2) | H | Me | Me | $CH_2CH_2$ | C=O(4) | O |
| S | (4-$CF_3$)Ph | Isobutyl | Me(2) | H | H | H | $CH_2CH_2$ | C=O(4) | O |
| S | (4-$CF_3$)Ph | Phenylethyl | Me(2) | H | H | H | $CH_2CH_2$ | C=O(4) | O |
| S | (4-$CF_3$)Ph | Isopropyl | $CF_3$(2) | H | H | H | $CH_2CH_2$ | C=O(4) | O |
| S | (4-$CF_3$)Ph | Isopropyl | $CHF_2$(2) | H | H | H | $CH_2CH_2$ | C=O(4) | O |
| S | (4-$CF_3$)Ph | Isopropyl | Me(2) | H | H | H | $CH_2CH_2$ | C=$CH_2$(4) | O |

Remark:
Numeral in ( ) means a position of the group.

(2) Compounds of the Following Formula

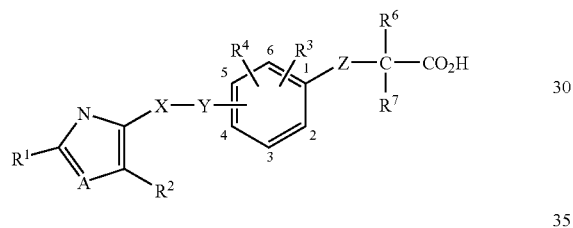

Compounds of the formula (I) in which $R^4$ is H, $R^5$ is H, B is CH, $R^8$ is H, and $R^1$, $R^2$, $R^3$, $R^6$, $R^7$, A, X, Y and Z are shown in Tables 5 and 6.

TABLE 5

| A | R¹ | R² | R³ | R⁴ | R⁶ | R⁷ | X | Y | Z |
|---|---|---|---|---|---|---|---|---|---|
| O | (2,4-Cl)Ph | Isopropyl | Me(2) | H | Me | Me | $CH_2CH_2$ | C=O(4) | O |
| O | (2,4-Cl)Ph | Isopropyl | Me(2) | H | H | H | $CH_2CH_2$ | C=O(4) | O |
| O | (2,4-Cl)Ph | Isopropyl | Allyl(2) | H | H | H | $CH_2CH_2$ | C=O(4) | O |
| O | (2-OH,4-Cl)Ph | Isopropyl | Me(2) | H | H | H | $CH_2CH_2$ | C=O(4) | O |
| O | (2-OH,4-Cl)Ph | Isopropyl | Me(2) | H | Me | Me | $CH_2CH_2$ | C=O(4) | O |
| O | (2,4-Cl)Ph | Isopropyl | Me(2) | H | H | H | $CH_2CH_2$ | C=O(4) | S |
| O | (2,4-Cl)Ph | Isopropyl | Me(2) | H | H | H | $CH_2CH_2$ | CH=CH(4) | O |
| O | (2,4-Cl)Ph | Isopropyl | Me(3) | H | H | H | $CH_2CH_2$ | C=O(4) | O |
| O | (2,4-Cl)Ph | Isopropyl | Me(3) | H | Me | Me | $CH_2CH_2$ | C=O(4) | O |
| O | (2,4-Cl)Ph | Isopropyl | Me(2) | H | H | H | $CH_2CH_2$ | C=$CH_2$(4) | O |
| O | (2,4-Cl)Ph | Isopropyl | Me(2) | H | Me | Me | $CH_2CH_2$ | C=$CH_2$(4) | O |
| O | (2,4-Cl)Ph | Isopropyl | Me(2) | H | H | H | $CH_2CH$(Me) | C=O(4) | O |
| O | (2,4-Cl)Ph | Isopropyl | Me(2) | H | Me | Me | $CH_2CH$(Me) | C=O(4) | O |
| O | (2,4-Cl)Ph | Isopropyl | Cl(2) | H | H | H | $CH_2CH_2$ | C=O(4) | O |
| O | (2,4-Cl)Ph | Isopropyl | Cl(2) | H | Me | Me | $CH_2CH_2$ | C=O(4) | O |
| S | (4-$CF_3$)Ph | Isopropyl | Me(2) | H | H | H | $CH_2CH_2$ | C=O(4) | O |
| S | (4-$CF_3$)Ph | Isopropyl | Me(2) | H | Me | Me | $CH_2CH_2$ | C=O(4) | O |
| S | (2,4-Cl)Ph | Isopropyl | Me(2) | H | H | H | $CH_2CH_2$ | C=O(4) | O |
| S | (2,4-Cl)Ph | Isopropyl | Me(2) | H | Me | Me | $CH_2CH_2$ | C=O(4) | O |
| O | (2,4-Me)Ph | Isopropyl | Pr(3) | H | Me | Me | CH(Me)$CH_2$ | C=O(4) | O |
| S | (2-OH,4-Me)Ph | Bu | Benzyl(2) | H | H | H | $CH_2CH_2$ | C=O(3) | O |
| NH | (2-OH,4-$CF_3$)Ph | Pr | Acetyl(2) | H | H | H | $CH_2CH_2$ | C=O(4) | O |
| N—Me | (2-OH,4-Cl)Ph | Hexyl | Cl(2) | H | H | H | $CH_2CH_2$ | C=O(4) | O |
| S | (2,4-Me)Ph | Et | Br(2) | H | H | H | $CH_2CH_2$ | C=O(4) | S |
| O | (3,4-Cl)Ph | Bu | $CF_3$(3) | H | Me | Et | $CH_2CH_2$ | C=O(4) | O |

Remark:
Numeral in ( ) means a position of the group.

TABLE 6

| A | R¹ | R² | R³ | R⁴ | R⁶ | R⁷ | X | Y | Z |
|---|---|---|---|---|---|---|---|---|---|
| O | (2,4-Me)Ph | Hexyl | Me(2) | Me(6) | Me | Me | CH(Me)CH₂ | C=O(4) | O |
| O | (2,4-Cl)Ph | Bu | Me(2) | Me(3) | H | H | CH₂CH₂ | C=O(4) | O |
| O | (2-OH,3,4-Me)Ph | Pr | Allyl(2) | H | H | H | CH₂CH₂ | CH=CH(4) | O |
| S | (2,4-F)Ph | Hexyl | Ph(2) | H | Me | Me | CH₂CH₂ | CH=CH(4) | O |
| NH | (3,4,5-Me)Ph | Et | Me(2) | H | H | H | CH₂CH₂ | C=O(4) | S |
| N—Me | (2-OH,3,4-Me)Ph | Bu | Me(3) | H | Me | Me | CH₂CH₂ | C=O(4) | O |
| S | (2-OH,4-CF₃)Ph | Isopropyl | Me(2) | Me(6) | H | H | CH₂CH₂ | C=O(3) | O |
| O | (2-Cl,4-OMe)Ph | Isopropyl | Me(2) | Me(6) | H | H | CH₂CH₂ | C=O(4) | O |
| O | (2-Cl,4-OPh)Ph | Isopropyl | Acetyl(2) | H | H | H | CH₂CH₂ | C=O(4) | O |
| O | 1-Naphthyl | Isopropyl | Cl(2) | H | H | H | CH₂ | CH=CH(4) | S |
| O | 2-Naphthyl | Isopropyl | Br(2) | H | Me | Et | CH(Me)CH₂ | C=O(4) | O |
| S | 2-Quinolyl | Isopropyl | CF₃(2) | H | Me | Me | CH₂CH₂ | C=O(4) | O |
| NH | 8-Quinolyl | Isopropyl | Me(2) | H | Me | Me | CH₂CH₂ | C=O(4) | O |
| N—Me | 3-Quinolyl | Isopropyl | Me(2) | H | H | H | CH₂CH₂ | C=O(4) | O |
| S | 2-Pyrimidyl | Isopropyl | Allyl(2) | H | H | H | CH₂CH₂ | C=O(4) | O |
| O | 2-Thienyl | Isopropyl | Me(2) | H | H | H | CH₂ | CH=CH(4) | S |
| O | 2-Furanyl | Isopropyl | Me(2) | H | H | H | CH₂CH₂ | C=O(4) | O |
| O | 2-Imidazolyl | Isopropyl | Me(2) | H | Me | Et | CH₂CH₂ | C=O(4) | O |
| O | 2-Indolyl | Isopropyl | Pr(2) | H | Me | Me | CH₂CH₂ | C=O(4) | O |
| O | 2-Benzofuranyl | Isopropyl | Benzyl(2) | H | Me | Me | CH₂CH₂ | C=O(4) | O |
| S | 2-Benzothienyl | Isopropyl | Acetyl(2) | H | Me | Me | CH₂CH₂ | C=O(4) | S |
| S | 2-Benzimidazolyl | Isopropyl | Cl(2) | Cl(6) | Me | Me | CH₂CH₂ | C=O(4) | S |

Remark:
Numeral in ( ) means a position of the group.

(3) Compounds of the Following Formula

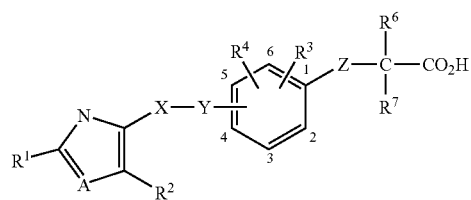

Compounds of the formula (I) in which $R^5$ is H, B is CH, $R^8$ is H, and $R^1$, $R^2$, $R^3$, $R^4$, $R^6$, $R^7$, A, X, Y and Z are shown in Table 7.

TABLE 7

| A | R¹ | R² | R³ | R⁴ | R⁶ | R⁷ | X | Y | Z |
|---|---|---|---|---|---|---|---|---|---|
| O | (2,4-Me)Ph | Hexyl | Me(2) | Me(6) | Me | Me | C=O(4) | CH(Me)CH₂ | O |
| O | (2,4-Cl)Ph | Bu | Me(2) | Me(3) | H | H | C=O(4) | CH₂CH₂ | O |
| S | (2-OH,4-CF₃)Ph | Isopr | Me(2) | Me(6) | H | H | C=O(3) | CH₂CH₂ | O |
| O | (2-Cl,4-OMe)Ph | Isopr | Me(2) | Me(6) | H | H | C=O(4) | CH₂CH₂ | O |
| S | 2-Benzimidazolyl | Isopr | Cl(2) | Cl(6) | Me | Me | C=O(4) | CH₂CH₂ | S |

Remark:
Numeral in ( ) means a position of the group.

The pharmacological effects of the invention are described below.

The PPARδ activating effect of the compound of the invention was determined by the following method:

A chimeric receptor expression plasmid (GAL4-hPPARδ LBD), a reporter plasmid (UASx4-TK-LUC) and β-galactosidase (β-GAL) are transfected into CV-1 cells by utilizing a lipofection reagent DMRIE-C (Life Technologies). Subsequently, it is incubated for 40 hours in the presence of a compound of the invention or a compound for comparison (L-165041), and then the luciferase activity and β-GAL activity are measured on the soluble cells.

The luciferase activity is calibrated by the β-GAL activity, and a relative ligand activity is calculated under the condition that the luciferase activity of the cells treated by L-165041 is set to 100%). In the same manner, relative ligand activities to PPARδ and γ transactivation activities are calculated (see the below-mentioned Examples 51, 52).

As seen from Tables 8, 9, the compounds of the invention (Examples 1-50) show an excellent PPARδ activating effect.

As also seen from Example 53 (Table 10), the compounds of the invention (Examples 4 and 10) show an excellent effect of increasing HDL cholesterol.

Apparently, the compounds of the invention having the general formula (I) show excellent PPARδ activating effect. Accordingly, these compounds are expected to serve as remedy for prevention and treatment of the following diseases: hyperglycemia, hyperlipidemia, obesity, syndrome X, hyperchloresterolemia, hyperlipopreoteinemia, other dysbolismic diseases, hiperlipemia, arterial sclerosis, diseases of cardiovascular systems, hyperphagia, ischemic diseases, malignant tumors such as lung cancer, mammary cancer, colonic cancer, cancer of great intestine, and ovary cancer, Alzheimer's disease, inflammatory disease, osteoporosis (Mano H. et al., (2000) J. Biol. Chem., 175:8126-8132), Basedow's disease, and adrenal cortical dystrophy.

The compound of the invention can be administered to human beings by ordinary administration methods such as oral administration or parenteral administration.

The compound can be granulated in ordinary manners for the preparation of pharmaceuticals. For instance, the compound can be processed to give pellets, granule, powder, capsule, suspension, injection, suppository, and the like.

For the preparation of these pharmaceuticals, ordinary additives such as vehicles, disintegrators, binders, lubricants, dyes, and diluents. As the vehicles, lactose, D-mannitol, crystalline cellulose and glucose can be mentioned. Further, there can be mentioned starch and carboxymethylcellulose calcium (CMC-Ca) as the disintegrators, magnesium stearate and talc as the lubricants, and hydroxypropylcellulose (HPC), gelatin and polyvinylpirrolidone (PVP) as the binders.

The compound of the invention can be administered to an adult generally in an amount of 0.1 mg to 100 mg a day by parenteral administration and 1 mg to 2,000 mg a day by oral administration. The dosage can be adjusted in consideration of age and conditions of the patient.

The invention is further described by the following non-limiting examples.

EXAMPLES

Example 1

2-[4-[3-[2-(2,4-Dichlorophenyl)-5-isopropyl-4-oxazolyl]propionyl]-2-methylphenoxy]-2-methylpropionic acid (1) 3-[2-(2,4-Dichlorophenyl)-5-isopropyl-4-oxazolyl]-1-(3-methyl-4-hydroxyphenyl)propan-1-one To an ice-cold THF (5 mL) was added 60% sodium hydride (97 mg, 2.42 mmol). Subsequently, a solution of ethyl 2-[(3-methyl-4-benzyloxy)benzoyl]acetate (757 mg, 2.42 mmol) in THF (4 mL) was dropwise added for 30 minutes. The mixture was allowed to room temperature, and then stirred for 30 minutes. To the mixture was added 4-iodomethyl-5-isopropyl-2-(2,4-dichlorophenyl)oxazole (960 mg, 2.42 mmol). The resulting mixture was refluxed for 20 hours under nitrogen atmosphere, and allowed to room temperature. THF was removed under reduced pressure. To the residue was added acetic acid (6.4 mL)-conc. hydrochloric acid (1.6 mL), and the mixture was refluxed for 10 hours, and allowed to room temperature. The reaction mixture was poured into ice water. Ethyl acetate was added to the mixture. The organic layer was washed with a saturated aqueous sodium hydrogen carbonate solution, water, and a saline, dried over anhydrous sodium sulfate. Ethyl acetate was removed under reduced pressure, and the residue was purified by column chromatography on silica gel with hexane/ethyl acetate (3/1) to give the desired compound (706 mg) as pale yellowish white crystalline (yield 70%).

$^1$H-NMR (CDCl$_3$, 400 MHz) δ: 1.30(d, 6H, J=7 Hz), 2.26(s, 3H), 2.95(t, 2H, J=7 Hz), 3.19(dq, 1H, J=7 Hz, J=7 Hz), 3.30(t, 2H, J=7 Hz), 5.75(s, 1H), 6.75(d, 1H, J=8 Hz), 7.30(dd, 1H, J=2, 8 Hz), 7.49(d, 1H, J=2 Hz), 7.70(dd, 1H, J=2, 8 Hz), 7.76(d, 1H, J=2 Hz), 7.88(d, 1H, J=8 Hz).

(2) Ethyl 2-[4-[3-[2-(2,4-dichlorophenyl)-5-isopropyl-4-oxazolyl]propionyl]-2-methylphenoxy]-2-methylpropionate In methyl ethyl ketone (10 mL) were suspended the obtained 3-[2-(2,4-dichlorophenyl)-5-isopropyl-4-oxazolyl]-1-(3-methyl-4-hydroxyphenyl)propan-1-one (209 mg, 0.50 mmol), ethyl 2-bromo-2-methylpropionate (489 mg, 2.50 mmol), and potassium carbonate (346 mg, 2.50 mmol). The suspension was refluxed for 40 hours. The suspension was then allowed to room temperature, filtered to remove insolubles, and washed with methyl ethyl ketone. The solvent was distilled off. The residue was purified by column chromatography on silica gel with hexane/ethyl acetate (7/1) to give the desired compound (272 mg) as colorless oil (quantitative yield).

$^1$H-NMR (CDCl$_3$, 400 MHz) δ: 1.26(t, 3H, J=7 Hz), 1.29(d, 6H, J=7 Hz), 1.64(s, 6H), 2.25(s, 3H), 2.95(t, 2H, J=7 Hz), 3.18(dq, 1H, J=7 Hz, J=7 Hz), 3.32(t, 2H, J=7 Hz), 4.21(q, 2H, J=7 Hz), 6.60(d, 1H, J=8 Hz), 7.30(dd, 1H, J=2, 8 Hz), 7.49(d, 1H, J=2 Hz), 7.71(dd, 1H, J=2, 8 Hz), 7.80(d, 1H, J=2 Hz), 7.89(d, 1H, J=8 Hz).

(3) 2-[4-[3-[2-(2,4-Dichlorophenyl)-5-isopropyl-4-oxazolyl]propionyl]-2-methylphenoxy]-2-methylpropionic acid In a mixture of ethanol (6 mL) and water (3 mL) was dissolved the obtained ester compound (270 mg, 0.51 mmol), and then lithium hydroxide monohydrate (65 mg) was added. The mixture was refluxed for 48 hours, and allowed to room temperature. Ice water was added to the reaction mixture. The mixture was neutralized by addition of 3N hydrochloric acid. Precipitated crystals were filtered, washed with water, dried in air over night, and further dried under reduced pressure (60° C.) to give 170 mg of the desired compound (yield 68%).

White powder (mp: 100-105° C.) $^1$H-NMR (CDCl$_3$, 400 MHz) δ: 1.30(d, 6H, J=7 Hz), 1.66(s, 6H), 2.24(s, 3H), 2.94(t, 2H, J=7 Hz), 3.21(dq, 1H, J=7 Hz, J=7 Hz), 3.26(t, 2H, J=7 Hz), 6.71(d, 1H, J=8 Hz), 7.29(dd, 1H, J=2, 8 Hz), 7.49(d, 1H, J=2 Hz), 7.56(dd, 1H, J=2, 8 Hz), 7.79(d, 1H, J=2 Hz), 7.84(d, 1H, J=8 Hz).

Example 2

[4-[3-[2-(2,4-Dichlorophenyl)-5-isopropyl-4-oxazolyl]propionyl]-2-methylphenoxy]acetic acid (1) Ethyl [4-[3-[2-(2,4-dichlorophenyl)-5-isopropyl-4-oxazolyl]propionyl]-2-methylphenoxy]acetate The synthetic intermediate of Example 1, namely 3-[2-(2,4-dichlorophenyl)-5-isopropyl-4-oxazolyl]-1-(3-methyl-4-hydroxyphenyl)propan-1-one (105 mg, 0.25 mmol) and potassium carbonate (103 mg, 0.75 mmol) were suspended in acetone (3 mL). Ethyl bromoacetate (0.08 mL, 0.75 mmol) was added to the suspension while cooling with ice. The suspension was allowed to room temperature, and refluxed while heating for 6 hours. Insolubles were filtered, and washed with acetone. Subsequently, the solvent was distilled off. The residue was purified by column chromatography on silica gel with hexane/ethyl acetate (7/1-4/1) to give the subject compound (117 mg) as colorless oil (yield 92%)

$^1$H-NMR (CDCl$_3$, 400 MHz) δ: 1.26(t, 3H, J=7 Hz), 1.30(d, 6H, J=7 Hz), 2.31(s, 3H), 2.75(t, 2H, J=7 Hz), 3.18(dq, 1H, J=7 Hz, J=7 Hz), 3.33(t, 2H, J=7 Hz), 4.26(q, 2H, J=7 Hz), 4.69(s, 2H), 6.69(d, 1H, J=8 Hz), 7.30(dd, 1H, J=2, 8 Hz), 7.49(d, 1H, J=2 Hz), 7.8-7.85(m, 2H), 7.89(d, 1H, J=8 Hz).

Example 3

[4-[3-[2-(4-Trifluoromethyl)phenyl-4-isopropyl-5-thiazolyl]propionyl]-2-methylphenoxy]acetic acid (1) 3-[2-(4-Trifluoromethyl)phenyl-4-isopropyl-5-thiazolyl]-1-(3-methyl-4-hydroxyphenyl)propan-1-one To an ice-cold THF (5 mL) was added 60% sodium hydride (27 mg, 0.67 mmol). Subsequently, a solution of ethyl 2-[(3-methyl-4-benzyloxy)benzoyl]acetate (190 mg, 0.61 mmol) in THF (3 mL) was dropwise added for 30 minutes. The mixture was allowed to room temperature, and then stirred for 30 minutes. To the mixture was added 5-iodomethyl-4-isopropyl-2-(4-trifluoromethyl)phenylthiazole (250 mg, 0.61 mmol). The resulting mixture was refluxed for 20 hours under nitrogen atmosphere, and allowed to room temperature. THF was removed under reduced pressure. To the residue was added acetic acid (3.2 mL)-conc. hydrochloric acid (0.8 mL), and the mixture was refluxed for 10 hours under heating, and allowed to room temperature. The reaction mixture was poured into ice water. The mixture was extracted with ethyl acetate. The organic layer was washed with a saturated aqueous sodium hydrogen carbonate solution, water, and a saline, dried over anhydrous sodium sulfate. Ethyl acetate was removed under reduced pressure, and the residue was purified by column chromatography on silica gel with hexane/ethyl acetate (3/1) to give the desired compound (195 mg) as pale yellowish white crystal (yield 73%).

$^1$H-NMR (CDCl$_3$, 400 MHz): 1.33(d, 6H, J=7 Hz), 2.29 (s, 3H), 3.14(dq, 1H, J=7 Hz, J=7 Hz), 3.2-3.3(m, 4H), 5.35(s, 1H), 6.80(d, 1H, J=8 Hz), 7.63(d, 2H, J=8 Hz), 7.74(dd, 1H, J=2, 8 Hz), 7.79(d, 1H, J=2 Hz), 7.89(d, 2H, J=8 Hz).

(2) Ethyl [4-[3-[2-(4-Trifluoromethyl)phenyl-4-isopropyl-5-thiazolyl]propionyl]-2-methylphenoxy]acetate The desired compound was obtained in an analogous manner as in (1) of Example 2 (yield 80%).

Colorless oil $^1$H-NMR (CDCl$_3$, 400 MHz) δ: 1.30(t, 3H, J=7 Hz), 1.33(d, 6H, J=7 Hz), 2.33(s, 3H), 3.15(dq, 1H, J=7 Hz, J=7 Hz), 3.2-3.3(m, 4H), 4.27(q, 2H, J=7 Hz), 4.71(s, 2H), 6.71(d, 1H, J=8 Hz), 7.64(d, 2H, J=8 Hz), 7.75(dd, 1H, J=2, 8 Hz), 7.81(d, 1H, J=2 Hz), 8.00(d, 2H, J=8 Hz).

(3) [4-[3-[2-(4-Trifluoromethyl)phenyl-4-isopropyl-5-thiazolyl]propionyl]-2-methylphenoxy]acetic acid The desired compound was obtained in an analogous manner as in (2) of Example 2 using the obtained ester compound (yield 88%).

White powder (mp: 145-155° C.) $^1$H-NMR (CDCl$_3$, 400 MHz) δ: 1.33(d, 6H, J=7 Hz), 2.32(s, 3H), 3.15(dq, 1H, J=7 Hz, J=7 Hz), 3.2-3.3(m, 4H), 4.76(s, 2H), 6.75(d, 1H, J=8 Hz), 7.64(d, 2H, J=8 Hz), 7.81(dd, 1H, J=2, 8 Hz), 7.82(d, 1H, J=2 Hz), 8.00(d, 2H, J=8 Hz).

Example 4

2-[4-[3-[2-(4-Trifluoromethyl)phenyl-4-isopropyl-5-thiazolyl]propionyl]-2-methylphenoxy]-2-methylpropionic acid (1) Ethyl 2-[4-[3-[2-(4-Trifluoromethyl)phenyl-4-isopropyl-5-thiazolyl]propionyl]-2-methylphenoxy]-2-methylpropionate The desired compound was obtained in an analogous manner as in (2) of Example 1 using the synthetic intermediate of Example 3, namely 3-[2-(4-trifluoromethyl)phenyl-4-isopropyl-5-thiazolyl]-1-(3-methyl-4-hydroxyphenyl)propan-1-one (yield 74%).

Colorless oil $^1$H-NMR (CDCl$_3$, 400 MHz) δ: 1.21(t, 3H, J=7 Hz), 1.33(d, 6H, J=7 Hz), 1.65(s, 6H), 2.27(s, 3H), 3.15(dq, 1H, J=7 Hz, J=7 Hz), 3.2-3.3(m, 4H), 4.22(q, 2H, J=7 Hz), 6.62(d, 1H, J=8 Hz), 7.64(d, 2H, J=8 Hz), 7.70(dd, 1H, J=2, 8 Hz), 7.80(d, 1H, J=2 Hz), 8.00(d, 2H, J=8 Hz).

(2) 2-[4-[3-[2-(4-Trifluoromethyl)phenyl-4-isopropyl-5-thiazolyl]propionyl]-2-methylphenoxy]-2-methylpropionic acid The desired compound was obtained in an analogous manner as in (3) of Example 1 using the obtained ester compound (yield 90%).

Pale yellow amorphous $^1$H-NMR (CDCl$_3$, 400 MHz) δ: 1.33(d, 6H, J=7 Hz), 1.67(s, 6H), 2.27(s, 3H), 3.14(dq, 1H, J=7 Hz, J=7 Hz), 3.2-3.3(m, 4H)., 6.75(d, 1H, J=8 Hz), 7.63(d, 2H, J=8 Hz), 7.72(dd, 1H, J=2, 8 Hz), 7.80(d, 1H, J=2 Hz), 7.99(d, 2H, J=8 Hz).

Example 5

[2-Allyl-4-[3-[2-(2,4-dichlorophenyl)-5-isopropyl-4-oxazolyl]propionyl]phenoxy]acetic acid (1) 3-[2-(2,4-Dichlorophenyl)-5-isopropyl-4-oxazolyl]-1-(4-hydroxyphenyl)propan-1-one To an ice-cold THF (15 mL) was added 60% sodium hydride (120 mg, 3.00 mmol). Subsequently, a solution of ethyl 2-[(4-benzyloxy)benzoyl]acetate (900 mg, 3.02 mmol) in THF (15 mL) was dropwise added for 30 minutes. The mixture was allowed to room temperature, and then stirred for 30 minutes. To the mixture was added 4-iodomethyl-5-isopropyl-2-(2,4-dichlorophenyl)oxazole (1.20 g, 3.00 mmol). The resulting mixture was refluxed for 20 hours under nitrogen atmosphere, and allowed to room temperature. THF was removed under reduced pressure. To the residue was added acetic acid (7.5 mL)-conc. hydrochloric acid (2.0 mL), and the mixture was refluxed for 5 hours, and allowed to room temperature. The reaction mixture was poured into ice water, and extracted with ethyl acetate. The organic layer was washed with a saturated aqueous sodium hydrogen carbonate solution, water, and a saline, dried over anhydrous sodium sulfate. Ethyl acetate was removed under reduced pressure, and the residue was purified by column chromatography on silica gel with hexane/ethyl acetate (3/1) to give the desired compound (650 mg) as pale yellowish white crystal (yield 53%).

$^1$H-NMR (CDCl$_3$, 400 MHz) δ: 1.32(d, 6H, J=7 Hz), 2.96(t. 2H, J=7 Hz), 3.22(dq, 1H, J=7 Hz, J=7 Hz), 3.25(t,

2H, J=7 Hz), 6.77(d, 2H, J=8 Hz), 7.29(dd, 1H.J=2, 8 Hz), 7.49(d, 1H, J=2 Hz), 7.60(s, 1H), 7.76(d, 2H, J=8 Hz), 7.84(d, 1H, J=8 Hz).

(2) 3-[2-(2,4-Dichlorophenyl)-5-isopropyl-4-oxazolyl]-1-(4-allyloxyphenyl)propan-1-one In acetone (5 mL), 3-[2-(2,4-dichlorophenyl)-5-isopropyl-4-oxazolyl]-1-(4-hydroxyphenyl)propan-1-one (202 mg, 0.50 mmol) and potassium carbonate (103 mg, 0.75 mmol) were suspended. Allyl bromide (91 mg, 0.75 mmol) was added to the suspension while cooling with ice. The suspension was stirred at room temperature for 20 hours. The reaction mixture was poured into water, and extracted with ethyl acetate. The organic layer was washed with water, and a saline, dried over anhydrous sodium sulfate. Ethyl acetate was removed under reduced pressure to give the subject compound (205 mg) as pale yellow solid residue (yield 92%).
$^1$H-NMR (CDCl$_3$, 400 MHz) δ: 1.30(d, 6H, J=7 Hz), 2.96(t, 2H.J=7 Hz), 3.18(dq, 1H.J=7 Hz, J=7 Hz), 3.34(t, 2H, J=7 Hz), 4.59(dt, 2H, J=2, 5 Hz), 5.25-5.35(m, 1H), 5.40-5.45(m, 1H), 5.95-6.10(m, 1H), 6.93(d, 2H, J=9 Hz), 7.29(dd, 1H, J=2, 8 Hz), 7.49(d, 1H, J=2 Hz), 7.89(d, 1H, J=8 Hz), 7.96(d, 2H, J=9 Hz).

(3) 3-[2-(2,4-Dichlorophenyl)-5-isopropyl-4-oxazolyl]-1-(3-allyl-4-hydroxyphenyl)propan-1-one At 180° C., 3-[2-(2,4-dichlorophenyl)-5-isopropyl-4-oxazolyl]-1-(4-allyloxyphenyl)propan-1-one (200 mg, 0.45 mmol) was heated for 5 hours. The compound was allowed to room temperature, the resulting compound was purified by column chromatography on silica gel with hexane/ethyl acetate (3/1) to give the desired compound (36 mg) as pale yellow oil (yield 18%).
$^1$H-NMR (CDCl$_3$, 400 MHz) δ: 1.30(d, 6H, J=7 Hz), 2.96(t, 2H, J=7 Hz), 3.18(dq, 1H, J=7 Hz, J=7 Hz), 3.33(t, 2H, J=7 Hz), 3.43(d, 2H, J=6 Hz), 5.1-5.2(m, 2H), 5.51(s, 1H), 5.85-6.1(m, 1H), 6.82(d, 1H, J=8 Hz), 7.29(dd, 1H, J=2, 8 Hz), 7.49(d, 1H, J=2 Hz), 7.79(d, 1H, d, J=2 Hz), 7.80(dd, 1H, J=2, 8 Hz), 7.88(d, 1H, J=8 Hz).

(4) [2-Allyl-4-[3-[2-(2,4-dichlorophenyl)-5-isopropyl-4-oxazolyl]propionyl]phenoxy]ethyl acetate The desired compound was obtained in an analogous manner as in (1) of Example 2 (yield 84%).
Colorless oil
$^1$H-NMR (CDCl$_3$, 400 MHz) δ: 1.29(t, 3H, J=7 Hz), 1.30(d, 6H, J=7 Hz), 2.96(t, 2H, J=7 Hz), 3.18(dq, 1H, J=7 Hz, J=7 Hz), 3.33(t, 2H, J=7 Hz), 3.47(d, 2H, J=6 Hz), 4.26(q, 2H, J=7 Hz), 4.69(s, 2H), 5.05-5.15(m, 2H), 5.95-6.10(m, 1H), 6.73(d, 1H, J=8 Hz), 7.30(dd, 1H, J=2, 8 Hz), 7.49(d, 1H, J=2 Hz), 7.83(d, 1H, J=2 Hz), 7.84(dd, 1H, J=2, 8 Hz), 7.88(d, 1H, J=8 Hz).

(5) [2-Allyl-4-[3-[2-(2,4-dichlorophenyl)-5-isopropyl-4-oxazolyl]propionyl]phenoxy]acetic acid The desired compound was obtained in an analogous manner as in (2) of Example 2 (yield 81%).
White powder (mp: 145-150° C.) $^1$H-NMR (CDCl$_3$, 400 MHz) δ: 1.30(d, 6H, J=7 Hz), 2.96(t, 2H, J=7 Hz), 3.19(dq, 1H, J=7 Hz, J=7 Hz), 3.32(t, 2H, J=7 Hz), 3.46(d, 2H, J=6 Hz), 4.71(s, 2H), 5.05-5.15(m, 2H), 5.95-6.10(m, 1H), 6.95 (d, 1H, J=8 Hz), 7.30(dd, 1H, J=2, 8 Hz), 7.49(d, 1H, J=2 Hz), 7.81(dd, 1H, J=2, 8 Hz), 7.83(d, 1H, J=2 Hz), 7.86(d, 1H, J=8 Hz).

Example 6

[4-[3-[2-(2-Hydroxy-4-chlorophenyl)-5-isopropyl-4-oxazolyl]propionyl]-2-methylphenoxy]acetic acid (1) 3-[2-(2-Methoxy4-chlorophenyl)-5-isopropyl-4-oxazolyl]-1-(3-methyl-4-hydroxyphenyl)propan-1-one To an ice-cold THF (50 mL) was added 60% sodium hydride (204 mg, 5.10 mmol). Subsequently, a solution of ethyl 2-[(3-methyl-4-benzyloxy)benzoyl]acetate (1.6 g, 5.12 mmol) in THF (25 mL) was dropwise added for 30 minutes. The mixture was allowed to room temperature, and then stirred for 30 minutes. To the mixture was added 4-iodomethyl-5-isopropyl-2-(2-methoxy-4-chlorophenyl)oxazole (2.00 g, 5.11 mmol). The resulting mixture was refluxed for 20 hours under nitrogen atmosphere, and allowed to room temperature. THF was removed under reduced pressure. To the residue was added acetic acid (16 mL)-conc. hydrochloric acid (4 mL), and the mixture was refluxed for 10 hours under heating. The mixture was allowed to room temperature, and poured into ice water. Ethyl acetate was added to the mixture. The organic layer was washed with a saturated aqueous sodium hydrogen carbonate solution, water, and a saline, dried over anhydrous sodium sulfate. Ethyl acetate was removed under reduced pressure, and the obtained residue was filtered, washed with an ether, and hexane to give the desired compound as white powder. Subsequently, the washings was concentrated, and the residue was filtered, washed with an ether, and hexane in the same manner as is mentioned above. The obtained powder was mixed with the previously obtained powder, and the mixed powder was dried under reduced pressure to give the desired compound (1.8 g) as pale yellowish white crystal (yield 70%).
$^1$H-NMR (CDCl$_3$, 400 MHz) δ: 1.32(d, 6H, J=7 Hz), 2.18(s, 3H), 2.91(t, 2H, J=7 Hz), 3.06(t, 2H, J=7 Hz), 3.18(dq, 1H, J=7 Hz, J=7 Hz), 3.87(s, 3H), 6.70(d, 1H, J=8 Hz), 6.99(d, 1H, J=2 Hz), 7.03(dd, 1H, J=2, 8 Hz), 7.41(dd, 1H, J=2, 8 Hz), 7.49(d, 1H, J=2 Hz), 7.83(d, 1H, J=8 Hz), 8.94(s, 1H).

(2) 3-[2-(2-Hydroxy-4-chlorophenyl)-5-isopropyl-4-oxazolyl]-1-(3-methyl-4-hydroxyphenyl)propan-1-one]

The obtained 3-[2-(2-methoxy4-chlorophenyl)-5-isopropyl-4-oxazolyl]-1-(3-methyl-4-hydroxyphenyl)propan-1-one (621 mg, 1.50 mmol) was suspended in methylene chloride (30 mL) and cooled with ice. To the suspension, a 1M methylene chloride solution of boron trichloride (BCl$_3$) (3.0 mL, 3.00 mmol) was dropwise added for 1 minute. The mixture was allowed to room temperature, stirred for 72 hours, and poured into ice water. Chloroform and saturated sodium hydrogen carbonate were added to the mixture. The organic layer was washed with water, and a saline, dried over anhydrous sodium sulfate. The chloroform was removed under reduced pressure. The residue was purified by column chromatography on silica gel with hexane/ethyl acetate (3/1) to give the desired compound (385 mg) as colorless oil (yield 64%).
$^1$H-NMR (CDCl$_3$, 400 MHz) δ: 1.31(d, 6H, J=7 Hz), 2.27(s, 3H), 2.94(t, 2H.J=7 Hz), 3.19(dq, 1H, J=7 Hz, J=7

Hz), 3.29(t, 2H, J=7 Hz), 5.22(s, 1H), 6.79(d, 1H, J=8 Hz), 6.90(dd, 1H, J=2, 8 Hz), 7.04(d, 1H, J=2 Hz), 7.68(d, 1H, J=8 Hz), 7.74(dd, 1H, J=2, 8 Hz), 7.78(d, 1H, J=2 Hz), 11.50(s, 1H).

(3) [4-[3-[2-(2-Hydroxy-4-chlorophenyl)-5-isopropyl-4-oxazolyl]propionyl]-2-methylphenoxy]ethyl acetate The obtained 3-[2-(2-hydroxy-4-chlorophenyl)-5-isopropyl-4-oxazolyl]-1-(3-methyl-4-hydroxyphenyl)propan-1-one (378 mg, 0.95 mmol) was dissolved in acetone (20 mL). To the solution, potassium carbonate (158 mg, 0.95 mmol) and ethyl bromoacetate (158 mg, 0.95 mmol) were added while cooling with ice. The mixture was allowed to room temperature, and stirred for 20 hours. After insoluble was filtered off, the mixture was washed with acetone to remove the solvent. The residue was purified by column chromatography on silica gel with hexane/ethyl acetate (4/1) to give the desired compound (315 mg) as white solid (yield 69%).

$^1$H-NMR (CDCl$_3$, 400 MHz) δ: 1.29(t, 3H, J=7 Hz), 1.31(d, 6H, J=7 Hz), 2.31(s, 3H), 2.94(t, 2H, J=7 Hz), 3.20(dq, 1H, J=7 Hz, J=7 Hz), 3.30(t, 2H, J=7 Hz), 4.26(q, 2H, J=7 Hz), 4.69(s, 2H), 6.70(d, 1H, J=8 Hz), 6.90(dd, 1H, J=2, 8 Hz), 7.04(d, 1H, J=2 Hz), 7.68(d, 1H, J=8 Hz), 7.75-7.85(m, 2H), 11.48(s, 1H).

(4) [4-[3-[2-(2-Hydroxy-4-chlorophenyl)-5-isopropyl-4-oxazolyl]propionyl]-2-methylphenoxy]acetic acid The desired compound was obtained in an analogous manner as in (2) of Example 2 (yield 87%).

White powder (mp: 159-161° C.) $^1$H-NMR (CDCl$_3$, 400 MHz) δ: 1.31(d, 6H, J=7 Hz), 2.31(s, 3H), 2.94(t, 2H, J=7 Hz), 3.19(dq, 1H, J=7 Hz, J=7 Hz), 3.30(t, 2H, J=7 Hz), 4.76(s, 2H), 6.74(d, 1H, J=8 Hz), 6.90(dd, 1H, J=2, 8 Hz), 7.04(d, 1H, J=2 Hz), 7.68(d, 1H, J=8 Hz), 7.80-7.85(m, 2H).

Example 7

[4-[3-[2-(2,4-Dichlorophenyl)-5-isopropyl-4-oxazolyl]propionyl]-2-methylphenylsulfanyl]acetic acid (1) 3-[2-(2,4-Dichlorophenyl)-5-isopropyl-4-oxazolyl]-1-[3-methyl-4-(dimethylthiocarbamoyloxy)phenyl]propan-1-one In dry dioxane (5 mL), 3-[2-(2,4-dichlorophenyl)-5-isopropyl-4-oxazolyl]-1-(3-methyl-4-hydroxyphenyl)propan-1-one (417 mg, 1.00 mmol) obtained in (1) of Example 1, 4-dimethylaminopyridine (12 mg, 0.10 mmol) and triethylamine (0.28 mL, 2.00 mmol). To the solution, dimethylthiocarbamoyl chloride (148 mg, 1.20 mmol) was added while cooling with ice. The reaction temperature was increased, and refluxed over night. The mixture was allowed to room temperature. To the mixture, 4-dimethylaminopyridine (12 mg, 0.10 mmol) and dimethylthiocarbamoyl chloride (148 mg, 1.20 mmol) were again added. The mixture was refluxed for 20 hours. The reaction mixture was allowed to room temperature, and poured into ice water. Ethyl acetate was added to the mixture. The organic layer was washed with water, and a saline, dried over anhydrous sodium sulfate. Ethyl acetate was removed under reduced pressure. The residue was purified by column chromatography on silica gel with hexane/ethyl acetate (3/1), and chloroform/methanol (100/1) to give the desired compound (170 mg) as a mixture with the starting materials.

(2) 3-[2-(2,4-Dichlorophenyl)-5-isopropyl-4-oxazolyl]-1-[3-methyl-4-(dimethylcarbamoylsulfanyl)phenyl]propan-1-one The obtained crude thiocarbamoyl compound (160 mg) was dissolved in n-tetradecane (10 mL). The solution was refluxed at the internal temperature of 250° C. for 8 hours. The mixture was allowed to room temperature. The reaction mixture was directly purified by column chromatography on silica gel with hexane/ethyl acetate (3/1) to give the desired compound (120 mg) as a pale yellow oil (two steps yield 24%).

$^1$H-NMR (CDCl$_3$, 400 MHz) δ: 1.31(d, 6H, J=7 Hz), 2.45(s, 3H), 2.97(t, 2H, J=7 Hz), 3.0-3.2(br, 6H), 3.19(dq, 1H, J=7 Hz, J=7 Hz), 3.38(t, 2H, J=7 Hz), 7.30(dd, 1H, J=2, 8 Hz), 7.48(d, 1H, J=2 Hz), 7.57(d, 1H, J=8 Hz), 7.78(dd, 1H, J=2, 8 Hz), 7.88(d, 1H, J=2 Hz), 7.89(d, 1H, J=8 Hz).

(3) 3-[2-(2,4-Dichlorophenyl)-5-isopropyl-4-oxazolyl]-1-(3-methyl-4-mercaptophenyl)propan-1-one The obtained carbamoyl compound (110 mg, 0.22 mmol) was dissolved in dry methanol (5 mL). To the solution, 0.5N MeONa (0.66 mL, 0.33 mmol) was added. The mixture was refluxed for 20 hours, and allowed to room temperature. The mixture was poured into ice water. The mixture was neutralized with 3N hydrochloric acid. Ethyl acetate was added to the mixture. The organic layer was washed with water, and a saline, dried over anhydrous sodium sulfate. Ethyl acetate was removed under reduced pressure to obtain the desired compound (80 mg) as pale yellow oil (yield 84%).

$^1$H-NMR (CDCl$_3$, 400 MHz) δ: 1.30(d, 6H, J=7 Hz), 2.34(s, 3H), 2.96(t, 2H, J=7 Hz), 3.18(dq, 1H, J=7 Hz, J=7 Hz), 3.34(t, 2H, J=7 Hz), 3.51(s, 1H), 7.2-7.3(m, 2H), 7.49(d, 1H, J=2 Hz), 7.66(dd, 1H, J=2, 8 Hz), 7.75(d, 1H, J=2 Hz), 7.88(d, 1H, J=8 Hz).

(4) Ethyl [4-[3-[2-(2,4-dichlorophenyl)-5-isopropyl-4-oxazolyl]propionyl]-2-methylphenylsulfanyl]acetate The desired compound was obtained in an analogous manner as in (1) of Example 2 (yield 89%).

Colorless oil $^1$H-NMR (CDCl$_3$, 400 MHz) δ: 1.25(t, 3H, J=7 Hz), 1.30(d, 6H, J=7 Hz), 2.39(s, 3H), 2.96(t, 2H, J=7 Hz), 3.18(dq, 1H, J=7 Hz, J=7 Hz), 3.35(t, 2H, J=7 Hz), 3.73(s, 2H), 4.20(q, 2H, J=7 Hz), 7.2-7.35(m, 2H), 7.49(d, 1H, J=2 Hz), 7.7-7.8(m, 2H), 7.88(d, 1H, J=8 Hz).

(5) [4-[3-[2-(2,4-dichlorophenyl)-5-isopropyl-4-oxazolyl]propionyl]-2-methylphenylsulfanyl]acetic acid The desired compound was obtained in an analogous manner as in (2) of Example 2 using the obtained ester compound (yield 71%).

White powder (mp: 140-145° C.) $^1$H-NMR (CDCl$_3$, 400 MHz) δ: 1.30(d, 6H, J=7 Hz), 2.39(s, 3H), 2.96(t, 2H.J=7 Hz), 3.19(dq, 1H, J=7 Hz, J=7 Hz), 3.32(t, 2H, J=7 Hz), 3.77(s, 2H), 7.2-7.35(m, 2H), 7.49(d, 1H, J=2 Hz), 7.7-7.8(m, 2H), 7.87(d, 1H, J=8 Hz).

Example 8

2-[4-[3-[2-(2-Hydroxy-4-chlorophenyl)-5-isopropyl-4-oxazolyl]propionyl]-2-methylphenoxy]-2-methylpropionic acid

(1) Ethyl 2-[4-[3-[2-(2-hydroxy-4-chlorophenyl)-5-isopropyl-4-oxazolyl]propionyl]-2-methylphenoxy]-2-methylpropionate In methyl ethyl ketone (10 mL), 3-[2-(2-hydroxy-4-chlorophenyl)-5-isopropyl-4-oxazolyl]-1-(3-methyl-4-hydroxyphenyl)propan-1-one (150 mg, 0.38 mmol), ethyl 2-bromo-2-methylpropionate (146 mg, 0.75 mmol) and potassium carbonate (103 mg, 0.75 mmol) were suspended. The suspension was refluxed for 20 hours, and allowed to room temperature. After insoluble was filtered off, the mixture was washed with methyl ethyl ketone to removed the solvent. The residue was purified by column chromatography on silica gel with hexane/ethyl acetate (8/1) to give the desired compound (83 mg) as colorless oil (yield 43%).

$^1$H-NMR (CDCl$_3$, 400 MHz) δ: 1.21(t, 3H, J=7 Hz), 1.31(d, 6H, J=7 Hz), 1.64(s, 6H), 2.25(s, 3H), 2.93(t, 2H, J=7 Hz), 3.19(dq, 1H, J=7 Hz, J=7 Hz), 3.28(t, 2H, J=7 Hz), 4.22(q, 2H, J=7 Hz), 6.60(d, 1H, J=9 Hz), 6.90(dd, 1H, J=2, 9 Hz), 7.04(d, 1H, J=2 Hz), 7.68(d, 1H, J=9 Hz), 7.70(dd, 1H, J=2, 9 Hz), 7.78(d, 1H, J=2 Hz), 11.48(s, 1H).

(2) 2-[4-[3-[2-(2-Hydroxy-4-chlorophenyl)-5-isopropyl-4-oxazolyl]propionyl]-2-methylphenoxy]-2-methylpropionic acid The desired compound was obtained in an analogous manner as in (3) of Example 2 using the obtained ester compound (yield 33%).

Pale white amorphous $^1$H-NMR (CDCl$_3$, 400 MHz) δ: 1.31(d, 6H, J=7 Hz), 1.68(s, 6H), 2.27(s, 3H), 2.94(t, 2H, J=7 Hz), 3.20(dq, 1H, J=7 Hz, J=7 Hz), 3.29(t, 2H, J=7 Hz), 6.77(d, 1H, J=9 Hz), 6.90(dd, 1H, J=2, 9 Hz), 7.04(d, 1H, J=2 Hz), 7.68(d, 1H, J=9 Hz), 7.74(dd, 1H, J=2, 9 Hz), 7.80(d, 1H, J=2 Hz).

Example 9

[4-[3-[2-(2,4-Dichlorophenyl)-5-isopropyl-4-oxazolyl]-1-propenyl]-2-methylphenoxy]acetic acid

(1) 4-[3-[2-(2,4-Dichlorophenyl)-5-isopropyloxazol-4-yl]-1-hydroxypropyl]-2-methylphenol To a solution of lithium aluminum hydride (92 mg, 2.42 mmol) in dry THF (20 mL), 3-[2-(2,4-dichlorophenyl)-5-isopropyloxazol-4-yl]-1-(4-hydroxy-3-methylphenyl)propan-1-one (1.01 g, 2.41 mmol) was gradually added while cooling with ice. The mixture was stirred for 1 hour, and further stirred at room temperature. The reaction mixture was again cooled with ice. To the mixture, a saturated aqueous sodium sulfate solution was dropwise added. After insoluble materials were filtered out, the solvent was removed under reduced pressure. The residue was extracted with ethyl acetate, washed with water (15 mL) containing a small amount of a 1M aqueous solution of hydrochloric acid, and dried over anhydrous sodium sulfate. The solvent was removed under reduced pressure to obtain the desired compound (997 mg) as ocher yellow crystal (yield 98%).

$^1$H-NMR (CDCl$_3$, 400 MHz) δ: 1.30(d, 3H, J=7 Hz), 1.31(d, 3H, J=7 Hz), 2.07(dt, 2H, J=7 Hz, 7 Hz), 2.24(s, 3H), 2.67(dt, 2H, J=2 Hz, 7 Hz), 3.07(m, 1H), 3.65(brs, 1H), 4.72(t, 2H, J=7 Hz), 5.06(s, 1H), 6.71(d, 1H, J=8 Hz), 7.06(dd, 11H, J=2 Hz, 8 Hz), 7.15(d, 1H, J=2 Hz), 7.30(dd, 1H, J=2 Hz, 8 Hz), 7.50(d, 1H, J=2 Hz), 7.91(d, 1H, J=8 Hz).

(2) 4-[3-[2-(2,4-Dichlorophenyl)-5-isopropyloxazol-4-yl]-1-propenyl]-2-methylphenol To the obtained phenol compound (840 mg, 2.00 mmol), DMSO (8 mL) was added. The mixture was stirred at 150° C. for 2 hours, and allowed to room temperature. Ethyl acetate (20 mL) was added to the mixture. The mixture was washed with water (20 mL), and then a saturated saline (20 mL). After the mixture was dried over anhydrous sodium sulfate, the solvent was removed under reduced pressure. The residue was recrystallized with ethyl acetate/hexane=1/10 (6.6 mL) to give the desired compound (58 mg) as pale yellow crystal (total yield 81%).

$^1$H-NMR (CDCl$_3$, 400 MHz) δ: 1.31(d, 6H, J=7 Hz), 2.22(s, 3H), 3.13(m, 1H), 3.45(dd, 2H, J=1 Hz, 6 Hz), 4.72(brs, 1H), 6.19(dt, 1H, J=6 Hz, 16 Hz), 6.37(d, 1H, J=16 Hz), 6.69(d, 1H, J=8 Hz), 7.06(d, 1H, J=8 Hz), 7.12(s, 1H), 7.30(dd, 1H, J=2 Hz, 8 Hz), 7.50(d, 1H, J=2 Hz), 7.93(d, 1H, J=8 Hz).

(3) Ethyl [4-[3-[2-(2,4-dichlorophenyl)-5-isopropyl-4-oxazolyl]-1-propenyl]-2-methylphenoxy]acetate The desired compound was obtained in an analogous manner as in (1) of Example 2.

$^1$H-NMR (CDCl$_3$, 400 MHz) δ: 1.29(t, 3H, J=7 Hz), 1.31(d, 6H, J=7 Hz), 2.27(s, 3H), 3.12(m, 1H), 3.46(dd, 2H, J=1 Hz, 6 Hz), 4.25(q, 2H, J=7 Hz), 4.61(s, 2H), 6.22(dt, 1H, J=6 Hz, 16 Hz), 6.39(d, 1H, J=16 Hz), 6.63(d, 1H, J=8 Hz), 7.10(dd, 1H, J=2 Hz, 8 Hz), 7.18(d, 1H, J=2 Hz), 7.30(dd, 1H, J=2 Hz, 8 Hz), 7.50(d, 1H, J=2 Hz), 7.94(d, 1H, J=8 Hz).

(4) [4-[3-[2-(2,4-Dichlorophenyl)-5-isopropyl-4-oxazolyl]-1-propenyl]-2-methylphenoxy]acetic acid The desired compound was obtained in an analogous manner as in (2) of Example 2.

Pale yellow crystal (mp: 143-144° C.) $^1$H-NMR (DMSO-d$_6$, 400 MHz) δ: 1.27(d, 6H, J=7 Hz), 2.17(s, 3H), 3.22(m, 1H), 3.43(d, 2H, J=6 Hz), 4.66(s, 2H), 6.21(dt, 1H, J=6 Hz, 16 Hz), 6.39(d, 1H, J=16 Hz), 6.74(d, 1H, J=8 Hz), 7.14(dd, 1H, J=2 Hz, 8 Hz), 7.22(d, 1H, J=2 Hz), 7.56(dd, 1H, J=2 Hz, 8 Hz), 7.78(d, 1H, J=2 Hz), 7.98(d, 1H, J=8 Hz). IR (KBr) cm$^{-1}$: 2968, 2931, 1734, 1564, 1502, 1458, 1387, 1242, 1203, 1138, 1119, 966, 804.

Example 10

[4-[3-[4-Isopropyl-2-(4-trifluoromethyl)phenyl-5-thiazolyl]-1-propenyl]-2-methylphenoxy]acetic acid

(1) Ethyl [4-[3-[4-isopropyl-2-(4-trifluoromethyl)phenyl-5-thiazolyl]-1-propenyl]-2-methylphenoxy]acetate The desired compound was obtained in an analogous manner as in Example 9.

$^1$H-NMR (CDCl$_3$, 400 MHZ) δ: 1.29(t, 3H, J=7 Hz), 1.34(d, 6H, J=7 Hz), 2.28(s, 3H), 3.12(m, 1H), 3.67(dd, 2H, J=1 Hz, 6 Hz), 4.26(q, 2H, J=7 Hz), 4.62(s, 2H), 6.17(dt, 1H, J=6 Hz, 16 Hz), 6.40(d, 1H, J=16 Hz), 6.65(d, 1H, J=8 Hz), 7.11(dd, 1H, J=2 Hz, 8 Hz), 7.19(d, 1H, J=2 Hz), 7.64(d, 2H, J=8 Hz), 8.01(d, 2H, J=8 Hz).

(2) [4-[3-[4-Isopropyl-2-(4-trifluoromethyl)phenyl-5-thiazolyl]-1-propenyl]-2-methylphenoxy]acetic acid The desired compound was obtained in an analogous manner as in (2) of Example 2.
Pale yellow powder (mp: 125-128° C.) $^1$H-NMR (CDCl$_3$, 400 MHz) δ: 1.34(d, 6H, J=7 Hz), 2.28(s, 3H), 3.13(m, 1H), 3.68(dd, 2H, J=1 Hz, 6 Hz), 4.68(s, 2H), 6.19(dt, 1H, J=6 Hz, 16 Hz), 6.40(d, 1H, J=16 Hz), 6.69(d, 1H, J=8 Hz), 7.13(dd, 1H, J=2 Hz, 8 Hz), 7.20(d, 1H, J=2 Hz), 7.64(d, 2H, J=8 Hz), 8.01(d, 2H, J=8 Hz). IR (KBr) cm$^{-1}$: 2974, 1751, 1506, 1325, 1252, 1225, 1169, 1136, 1122, 1119, 1066, 843.

Example 11

[4-[3-[4-Hexyl-2-(4-trifluoromethyl)phenyl-5-thiazolyl]propionyl]-2-methylphenoxy]acetic acid

(1) Ethyl [4-[3-[4-hexyl-2-(4-trifluoromethyl)phenyl-5-thiazolyl]propionyl]-2-methylphenoxy]acetate The desired compound was obtained in an analogous manner as in (1) of Example 2.
$^1$H-NMR (CDCl$_3$, 400 MHz) δ: 0.89(t, 3H, J=7 Hz), 1.29(t, 3H, J=7 Hz), 1.3-1.5(m, 6H), 1.7-1.8(m, 2H), 2.33(s, 3H), 2.75(t, 2H, J=8 Hz), 3.2-3.3(m, 4H), 4.27(q, 2H, J=7 Hz), 4.71(s, 2H), 6.72(d, 1H, J=8 Hz), 7.64(d, 2H, J=8 Hz), 7.8-7.9(m, 2H), 7.97(dd, 2H, J=1 Hz, 8 Hz).

(2) [4-[3-[4-Hexyl-2-(4-trifluoromethyl)phenyl-5-thiazolyl]propionyl]-2-methylphenoxy]acetic acid The desired compound was obtained in an analogous manner as in (2) of Example 2.
Yellow amorphous
$^1$H-NMR (CDCl$_3$, 400 MHz) δ: 0.88(t, 3H, J=7 Hz), 1.3-1.5(m, 6H), 1.7-1.8(m, 2H), 2.32(s, 3H), 2.75(t, 2H, J=8 Hz), 3.2-3.3(m, 4H), 4.76(s, 2H), 6.75(d, 1H, J=8 Hz), 7.64(d, 2H, J=8 Hz), 7.7-7.9(m, 2H), 7.97(dd, 2H, J=1 Hz, 8 Hz). IR (KBr) cm$^{-1}$: 2954, 2929, 2858, 1724, 1676, 1603, 1500, 1441, 1327, 1284, 1219, 1169, 1142, 1111, 1068.

Example 12

2-[4-[3-[4-Hexyl-2-(4-trifluoromethyl)phenyl-5-thiazolyl]propionyl]-2-methylphenoxy]-2-methylpropionic acid

(1) Ethyl 2-[4-[3-[4-hexyl-2-(4-trifluoromethyl)phenyl-5-thiazolyl]propionyl]-2-methylphenoxy]-2-methylpropionate The desired compound was obtained in an analogous manner as in (2) of Example 1.
$^1$H-NMR (CDCl$_3$, 400 MHz) δ: 0.89(t, 3H, J=7 Hz), 1.21(t, 3H, J=7 Hz), 1.2-1.5(m, 6H), 1.65(s, 6H), 1.7-1.8(m, 2H), 2.27(s, 3H), 2.74(t, 2H, J=8 Hz), 3.2-3.3(m, 4H), 4.22(q, 2H, J=7 Hz), 6.62(d, 1H, J=8 Hz), 7.64(d, 2H, J=8 Hz), 7.70(dd, 2H, J=2 Hz, 8 Hz), 7.80(d, 1H, J=2 Hz), 7.98(d, 2H, J=8 Hz).

(2) 2-[4-[3-[4-Hexyl-2-(4-trifluoromethyl)phenyl-5-thiazolyl]propionyl]-2-methylphenoxy]-2-methylpropionic acid The desired compound was obtained in an analogous manner as in (3) of Example 1.
Yellow oil
$^1$H-NMR (CDCl$_3$, 400 MHz) δ: 0.88(t, 3H, J=7 Hz), 1.3-1.5(m, 6H), 1.6-1.8(m, 2H), 1.69(s, 6H), 2.27(s, 3H), 2.74(t, 2H, J=8 Hz), 3.2-3.3(m, 4H), 6.75(d, 1H, J=8 Hz), 7.63(d, 2H, J=8 Hz), 7.72(dd, 1H, J=2 Hz, 8 Hz), 7.80(d, 1H, J=2 Hz), 7.97(d, 2H, J=8 Hz). IR (KBr) cm$^{-1}$: 2956, 2927, 2858, 1741, 1678, 1601, 1500, 1325, 1261, 1169, 1124, 1066, 845.

Example 13

2-[4-[3-[4-Isopropyl-2-(4-trifluoromethyl)phenyl-5-thiazolyl]-1-propenyl]-2-methylphenoxy]-2-methylpropionic acid

(1) Ethyl 2-[4-[3-[4-Isopropyl-2-(4-trifluoromethyl)phenyl-5-thiazolyl]-1-propenyl]-2-methylphenoxy]-2-methylpropionate The desired compound was obtained in an analogous manner as in (2) of Example 1.
$^1$H-NMR (CDCl$_3$, 400 MHz) δ: 1.25(t, 3H, J=7 Hz), 1.34(d, 6H, J=7 Hz), 1.55(s, 6H), 2.21(s, 3H), 3.12(m, 1H), 3.67(dd, 2H, J=1 Hz, 6 Hz), 4.24(q, 2H, J=7 Hz), 6.17(dt, 1H, J=6 Hz, 16 Hz), 6.38(d, 1H, J=16 Hz), 6.60(d, 1H, J=8 Hz), 7.03(dd, 1H, J=2 Hz, 8 Hz), 7.16(d, 1H, J=2 Hz), 7.64(d, 2H, J=8 Hz), 8.01(d, 2H, J=8 Hz).

(2) 2-[4-[3-[4-Isopropyl-2-(4-trifluoromethyl)phenyl-5-thiazolyl]-1-propenyl]-2-methylphenoxy]-2-methylpropionic acid The desired compound was obtained in an analogous manner as in (3) of Example 1.
Yellow oil
$^1$H-NMR (CDCl$_3$, 400 MHz) δ: 1.34(d, 6H, J=7 Hz), 1.61(s, 6H), 2.23(s, 3H), 3.13(m, 1H), 3.68(dd, 2H, J=1 Hz, 6 Hz), 6.20(dt, 1H, J=6 Hz, 16 Hz), 6.40(d, 1H, J=16 Hz), 6.77(d, 1H, J=8 Hz), 7.09(dd, 1H, J=2 Hz, 8 Hz), 7.19(d, 1H, J=2 Hz), 7.64(d, 2H, J=8 Hz), 8.01(d, 2H, J=8 Hz). IR (KBr) cm$^{-1}$: 2970, 2929, 2872, 1716, 1616, 1500, 1325, 1167, 1126, 1066, 964, 845.

Example 14

[4-[3-[4-Isopropyl-2-(4-trifluoromethyl)phenyl-5-thiazolyl]propionyl]-3-methylphenoxy]acetic acid

(1) Ethyl [4-[3-[4-isopropyl-2-(4-trifluoromethyl)phenyl-5-thiazolyl]propionyl]-3-methylphenoxy]acetate The desired compound was obtained in an analogous manner as in (1) of Example 2.
$^1$H-NMR (CDCl$_3$, 400 MHz) δ: 1.30(t, 3H, J=7 Hz), 1.33(d, 6H, J=7 Hz), 2.56(s, 3H), 3.15(m, 1H), 3.23(s, 4H), 4.28(q, 2H, J=7 Hz), 4.65(s, 2H), 6.75(dd, 1H, J=2 Hz, 9 Hz), 6.78(d, 1H, J=2 Hz), 7.64(d, 2H, J=9 Hz), 7.70(d, 1H, J=9 Hz), 8.00(d, 2H, J=9 Hz).

(2) [4-[3-[4-Isopropyl-2-(4-trifluoromethyl)phenyl-5-thiazolyl]propionyl]-3-methylphenoxy]acetic acid The desired compound was obtained in an analogous manner as in (2) of Example 2.
White crystal (mp: 136-142° C.) $^1$H-NMR (CDCl$_3$, 400 MHz) δ: 1.33(d, 6H, J=7 Hz), 2.56(s, 3H), 3.15(m, 1H), 3.23(s, 4H), 4.72(s, 2H), 6.7-6.8(m, 2H), 7.64(d, 2H, J=8 Hz), 7.71(d, 1H, J=9 Hz), 8.00(d, 2H, J=8 Hz). IR (KBr) cm$^{-1}$: 2962, 1741, 1672, 1603, 1574, 1450, 1325, 1260, 1236, 1211, 1168, 1126, 1066, 976, 849, 698, 611.

Example 15

[4-[3-[2-(2,4-Dichlorophenyl)-5-isopropyl-4-oxazolyl]propionyl]-3-methylphenoxy]acetic acid (1) Ethyl [4-[3-[2-(2,4-dichlorophenyl)-5-isopropyl-4-oxazolyl]propionyl]-3-methylphenoxy]acetate The desired compound was obtained in an analogous manner as in (1) of Example 2.
$^1$H-NMR (CDCl$_3$, 400 MHz) δ: 1.30(t, 3H, J=7 Hz), 1.30(d, 6H, J=7 Hz), 2.53(s, 3H), 2.94(t, 2H, J=7 Hz), 3.19(m, 1H), 3.29(t, 2H, J=7 Hz), 4.27(q, 2H, J=7 Hz), 4.64(s, 2H), 6.72(dd, 1H, J=2 Hz, 8 Hz), 6.76(d, 1H, J=2 Hz), 7.30(dd, 1H, J=2, 9 Hz), 7.49(d, 1H, J=2 Hz), 7.76(d, 1H, J=9 Hz), 7.88(d, 1H, J=8 Hz).

(2) [4-[3-[2-(2,4-Dichlorophenyl)-5-isopropyl-4-oxazolyl]propionyl]-3-methylphenoxy]acetic acid The desired compound was obtained in an analogous manner as in (2) of Example 2.
White crystal (mp: 97-102° C.) $^1$H-NMR (CDCl$_3$, 400 MHz) δ: 1.30(d, 6H, J=7 Hz), 2.51(s, 3H), 2.93(t, 2H, J=7 Hz), 3.19(m, 1H), 3.26(t, 2H, J=7 Hz), 4.65(s, 2H), 6.71(dd, 1H, J=2 Hz, 8 Hz), 6.75(d, 1H, J=2 Hz), 7.29(dd, 1H, J=2 Hz, 8 Hz), 7.48(d, 1H, J=2 Hz), 7.72(d, 1H, J=8 Hz), 7.85(d, 1H, J=8 Hz). IR (KBr) cm$^{-1}$: 3454, 2976, 1730, 1682, 1637, 1605, 1564, 1460, 1383, 1363, 1317, 1242, 1201, 1178, 1120, 1072, 1051, 978, 868, 818, 741.

Example 16

[4-[3-[4-Isopropyl-2-(4-trifluoromethyl)phenyl-5-thiazolyl]propionyl]-3-methylphenoxy]-2-methylpropionic acid (1) Ethyl [4-[3-[4-isopropyl-2-(4-trifluoromethyl)phenyl-5-thiazolyl]propionyl]-3-methylphenoxy]-2-methylpropionate The desired compound was obtained in an analogous manner as in (2) of Example 1.
$^1$H-NMR (CDCl$_3$, 400 MHz) δ: 1.22(t, 3H, J=7 Hz), 1.33(d, 6H, J=7 Hz), 1.63(s, 6H), 2.52(s, 3H), 3.14(m, 1H), 3.22(s, 4H), 4.22(q, 2H, J=7 Hz), 6.63(dd, 1H, J=2 Hz, 9 Hz), 6.90(d, 1H, J=2 Hz), 7.64(d, 1H, J=9 Hz), 7.64(d, 2H, J=9 Hz), 8.00(d, 2H, J=9 Hz).

(2) [4-[3-[4-Isopropyl-2-(4-trifluoromethyl)phenyl-5-thiazolyl]propionyl]-3-methylphenoxy]-2-methylpropionic acid The desired compound was obtained in an analogous manner as in (3) of Example 1.
Yellow amorphous
$^1$H-NMR (CDCl$_3$, 400 MHz) δ: 1.33(d, 6H, J=7 Hz), 1.66(s, 6H), 2.53(s, 3H), 3.14(m, 1H), 3.23(s, 4H), 6.74(dd, 1H, J=2 Hz, 8 Hz), 6.78(d, 1H, J=2 Hz), 7.64(d, 2H, J=8 Hz), 7.66(d, 1H, J=8 Hz), 8.00(d, 2H, J=8 Hz). IR (KBr) cm$^{-1}$: 3456, 2968, 2929, 2873, 1740, 1736, 1678, 1603, 1325, 1248, 1167, 1126, 1066.

Example 17

2-[4-[3-[2-(2,4-Dichlorophenyl)-5-isopropyl-4-oxazolyl]propionyl]-3-methylphenoxy]-2-methylpropionic acid (1) Ethyl 2-[4-[3-[2-(2,4-dichlorophenyl)-5-isopropyl-4-oxazolyl]propionyl]-3-methylphenoxy]-2-methylpropionate The desired compound was obtained in an analogous manner as in (2) of Example 1.
$^1$H-NMR (CDCl$_3$, 400 MHz) δ: 1.22(t, 3H, J=7 Hz), 1.30(d, 6H, J=7 Hz), 1.63(s, 6H), 2.49(s, 3H), 2.93(t, 2H, J=7 Hz), 3.18(m, 1H), 3.28(t, 2H, J=7 Hz), 4.23(q, 2H, J=7 Hz), 6.61(dd, 1H, J=2 Hz, 9 Hz), 6.67(d, 1H, J=2 Hz), 7.30(dd, 1H, J=2 Hz, 9 Hz), 7.49(d, 1H, J=2 Hz), 7.70(d, 1H, J=9 Hz), 7.88(d, 1H, J=9 Hz)

(2) 2-[4-[3-[2-(2,4-Dichlorophenyl)-5-isopropyl-4-oxazolyl]propionyl]-3-methylphenoxy]-2-methylpropionic acid The desired compound was obtained in an analogous manner as in (3) of Example 1.
White crystal (mp: 98-100° C.) $^1$H-NMR (CDCl$_3$, 400 MHz) δ: 1.30(d, 6H, J=7 Hz), 1.63(s, 6H), 2.47(s, 3H), 2.92(t, 2H, J=7 Hz), 3.1-3.3(m, 3H), 6.66(dd, 1H, J=2 Hz, 9 Hz), 6.73(d, 1H, J=2 Hz), 7.27(dd, 1H, J=2 Hz, 8 Hz), 7.48(d, 1H, J=2 Hz), 7.55(d, 1H, J=9 Hz), 7.83(d, 1H, J=8 Hz). IR (KBr) cm$^{-1}$: 2980, 2940, 1720, 1680, 1600, 1560, 1460, 1250, 1145, 1125.

Example 18

[4-[3-[4-Isopropyl-2-(4-trifluoromethyl)phenyl-5-thiazolyl]propionyl]-2-propylphenoxy]acetic acid (1) Ethyl 2-allyl-4-[3-[4-isopropyl-2-(4-trifluoromethyl)phenyl-5-thiazolyl]propionyl]phenoxyacetate The desired compound was obtained in an analogous manner as in (2), (3) and (4) of Example 5.
$^1$H-NMR (CDCl$_3$, 400 MHz) δ: 1.29(t, 3H, J=7 Hz), 1.33(d, 6H, J=7 Hz), 3.15(m, 1H), 3.2-3.3(m, 4H), 3.48(d, 2H, J=7 Hz), 4.26(q, 2H, J=7 Hz), 4.71(s, 2H), 5.1-5.2(m, 2H), 5.9-6.1(m, 1H), 6.75(d, 1H, J=9 Hz), 7.64(d, 2H, J=8 Hz), 7.8-7.9(m, 2H), 8.00(d, 2H, J=8 Hz).

(2) Ethyl [4-[3-[4-isopropyl-2-(4-trifluoromethyl)phenyl-5-thiazolyl]propionyl]-2-propylphenoxy]acetate $^1$H-NMR (CDCl$_3$, 400 MHz) δ: 0.95(t, 3H, J=7 Hz), 1.28(t, 3H, J=7 Hz), 1.33(d, 6H, J=7 Hz), 1.6-1.8(m, 2H), 2.68(t, 2H, J=7 Hz), 3.15(dq, 1H, J=7 Hz, 7 Hz), 3.2-3.3(m, 4H), 4.26(q, 2H, J=7 Hz), 4.70(s, 2H), 6.72(d, 1H, J=9 Hz), 7.64(d, 2H, J=8 Hz), 7.7-7.9(m, 2H), 8.00(d, 2H, J=8 Hz).

(3) [4-[3-[4-Isopropyl-2-(4-trifluoromethyl)phenyl-5-thiazolyl]propionyl]-2-propylphenoxy]acetic acid The desired compound was obtained in an analogous manner as in (2) of Example 2.
Pale white crystal (mp: 145-150° C.) $^1$H-NMR (CDCl$_3$, 400 MHz) δ: 0.96(t, 3H, J=7 Hz), 1.33(d, 6H, J=7 Hz), 1.6-1.8(m, 2H), 2.68(t, 2H, J=7 Hz), 3.15(dq, 1H, J=7 Hz, 7 Hz), 3.2-3.3(m, 4H), 4.77(s, 2H), 6.76(d, 1H, J=9 Hz), 7.64(d, 2H, J=8 Hz), 7.7-7.9(m, 2H), 8.00(d, 2H, J=8 Hz).

Example 19

2-Allyl-4-[3-[4-isopropyl-2-(4-trifluoromethyl)phenyl-5-thiazolyl]propionyl]phenoxyacetic acid The desired compound was obtained in an analogous manner as in (2) of Example 2.
Pale yellow crystal (mp: 165-175° C.) $^1$H-NMR (CDCl$_3$, 400 MHz) δ: 1.33(d, 6H, J=7 Hz), 3.15(dq, 1H, J=7 Hz, 7 Hz), 3.2-3.4(m, 4H), 3.48(d, 2H, J=7 Hz), 4.76(s, 2H), 5.0-5.1(m, 2H), 5.9-6.1(m, 1H), 6.79(d, 1H, J=9 Hz), 7.64(d, 2H, J=8 Hz), 7.8-7.9(m, 2H), 8.00(d, 2H, J=8 Hz).

Example 20

[4-[4-[2-(2,4-Dichlorophenyl)-5-isopropyl-4-oxazolyl]-1-buten-2-yl]-2-methylphenoxy]acetic acid (1) Ethyl [4-[4-[2-(2,4-dichlorophenyl)-5-isopropyl-4-oxazolyl]-1-buten-2-yl]-2-methylphenoxy]acetate In a dry ether (2 mL), potassium t-butoxide (120 mg, 1.07 mmol) was suspended. Methyl triphenyl phosphonium bromide (350 mg, 0.98 mmol) was added to the suspension. The mixture was stirred for 2 hours at room temperature. [4-[3-[2-(2,4-dichlorophenyl)-5-isopropyl-4-oxazolyl]propionyl]-2-methylphenoxy]ethyl acetate (450 mg, 0.89 mmol) and a dry ether (1.5 mL) were added to the mixture. The resulting mixture was stirred for 16 hours at room temperature. Methyl triphenyl phosphonium bromide (175 mg, 0.49 mmol), a dry ether (5 mL) and potassium t-butoxide (60 mg, 0.53 mmol) were added to the reaction mixture. The resulting mixture was stirred for 30 minutes at room temperature. The mixture was refluxed for 4 hours, and allowed to room temperature. Ethyl acetate (10 mL) was added to the reaction mixture. The mixture was washed with water (10 mL), and a saturated saline (10 mL), and dried over anhydrous sodium sulfate. The solvent was removed under reduced pressure. The residue was purified by column chromatography on silica gel with ethyl acetate/hexane (1/9) to give the desired compound (131 g) as colorless oil (yield 29%).
$^1$H-NMR (CDCl$_3$, 400 MHz) δ: 1.24(d, 6H, J=7 Hz), 1.30(t, 3H, J=7 Hz), 2.29(s, 3H), 2.6-2.7(m, 2H), 2.8-3.0(m, 3H), 3.27(q, 2H, J=7 Hz), 4.63(s, 2H), 5.00(d, 1H, J=1 Hz), 5.23(d, 1H, J=1 Hz), 7.66(d, 1H, J=8 Hz), 8.21(dd, 1H, J=2 Hz, 8 Hz), 7.26(d, 1H, J=2 Hz), 7.31(dd, 1H, J=2 Hz, 8 Hz), 7.50(d, 1H, J=2 Hz), 7.92(d, 1H, J=8 Hz).

(2) [4-[4-[2-(2,4-Dichlorophenyl)-5-isopropyl-4-oxazolyl]-1-buten-2-yl]-2-methylphenoxy]acetic acid The desired compound was obtained in an analogous manner as in (2) of Example 2.
Pale yellow oil
$^1$H-NMR (CDCl$_3$, 400 MHz) δ: 1.25(d, 6H, J=7 Hz), 2.29(s, 3H), 2.6-2.7(m, 2H), 2.8-2.9(m, 2H), 2.93(m, 1H), 4.65(s, 2H), 5.01(d, 1H, J=1 Hz), 5.23(d, 1H, J=1 Hz), 6.69(d, 1H, J=8 Hz), 7.22(dd, 1H, J=2 Hz, 8 Hz), 7.26(d, 1H, J=2 Hz), 7.32(dd, 1H, J=2 Hz, 8 Hz), 7.50(d, 1H, J=2 Hz), 7.91(d, 1H, J=8 Hz). IR (KBr) cm$^{-1}$: 3088, 2968, 2927, 2872, 1736, 1605, 1564, 1504, 1460, 1225, 1142, 1107.

Example 21

2-[4-[4-[2-(2,4-Dichlorophenyl)-5-isopropyl-4-oxazolyl]-1-buten-2-yl]-2-methylphenoxy]-2-methylpropionic acid (1) Ethyl 2-[4-[4-[2-(2,4-dichlorophenyl)-5-isopropyl-4-oxazolyl]-1-buten-2-yl]-2-methylphenoxy]-2-methylpropionate The desired compound was obtained in an analogous manner as in (2) of Example 1.
$^1$H-NMR (CDCl$_3$, 400 MHz) δ: 1.23(d, 6H, J=7 Hz), 1.26(t, 3H, J=7 Hz), 1.59(s, 6H), 2.30(s, 3H), 2.6-2.7(m, 2H), 2.8-3.0(m, 3H), 3.25(q, 2H, J=7 Hz), 4.99(d, 1H, J=1 Hz), 5.23(d, 1H, J=1 Hz), 6.62(d, 1H, J=8 Hz), 7.13(dd, 2H, J=1 Hz, 8 Hz), 7.24(d, 1H, J=2 Hz), 7.31(dd, 1H, J=2 Hz, 8 Hz), 7.50(d, 1H, J=2 Hz), 7.92(d, 1H, J=8 Hz).

(2) 2-[4-[4-[2-(2,4-Dichlorophenyl)-5-isopropyl-4-oxazolyl]-1-buten-2-yl]-2-methylphenoxy]-2-methylpropionic acid The desired compound was obtained in an analogous manner as in (3) of Example 1.
Brown oil
$^1$H-NMR (CDCl$_3$, 400 MHz) δ: 1.24(d, 6H, J=7 Hz), 1.61(s, 6H), 2.24(s, 3H), 2.6-2.7(m, 2H), 2.8-2.9(m, 2H), 2.91(m, 1H), 5.03(d, 1H, J=1 Hz), 5.25(d, 1H, J=1 Hz), 6.79(d, 1H, J=8 Hz), 7.18(dd, 1H, J=2 Hz, 8 Hz), 7.26(m, 1H), 7.31(dd, 1H, J=2 Hz, 8 Hz), 7.50(d, 1H, J=2 Hz), 7.91(d, 1H, J=8 Hz). IR (KBr) cm$^{-1}$: 2972, 2935, 2873, 1716, 1603, 1564, 1500, 1464, 1385, 1250, 1151, 1107.

Example 22

[4-[3-[2-(2,4-Dichlorophenyl)-5-isopropyl-4-oxazolyl]-2-methylpropionyl]-2-methylphenoxy]acetic acid (1) Ethyl [4-[3-[2-(2,4-dichlorophenyl)-5-isopropyl-4-oxazolyl]-2-methylpropionyl]-2-methylphenoxy]acetate Ethyl [4-[3-[2-(2,4-dichlorophenyl)-5-isopropyl-4-oxazolyl]propionyl]-2-methylphenoxy]acetate (450 mg, 0.89 mmol) was dissolved in dry THF (4 mL). Sodium hydride (40 mg, 1.00 mmol) was gradually added to the solution. The mixture was stirred for 30 minutes at room temperature. Methyl iodide (0.07 mL, 1.12 mmol) was dropwise added to the mixture. The resulting mixture was stirred for 27 hours at room temperature. Sodium hydride (10 mg, 0.25 mmol) and methyl iodide (0.02 mL, 0.32 mmol) were further added to the mixture. The resulting mixture was stirred for 19 hours 30 minutes at room temperature. The solvent was removed under reduced pressure. Ethyl acetate (5 mL) was added to the residue. The residue was washed with a saturated saline (2 mL), and dried over anhydrous sodium sulfate. The solvent was removed under reduced pressure. The residue was purified by column chromatography on silica gel with ethyl acetate/hexane (1/9) to give the desired compound (218 mg) as colorless oil (purity 97%, yield 29%).

$^1$H-NMR (CDCl$_3$, 400 MHz) δ: 1.18(d, 3H, J=7 Hz), 1.22(d, 3H, J=7 Hz), 1.28(d, 3H, J=7 Hz), 1.29(t, 3H, J=7 Hz), 2.29(s, 3H), 2.63(dd, 1H, J=7 Hz, 14 Hz), 3.00(dd, 1H, J=7 Hz, 14 Hz), 3.10(m, 1H), 4.00(m, 1H), 4.26(q, 2H, J=7 Hz), 4.68(s, 2H), 6.67(d, 1H, J=8 Hz), 7.30(dd, 1H, J=2 Hz, 8 Hz), 7.48(d, 1H, J=2 Hz), 7.8-7.9(m, 2H), 7.85(d, 1H, J=8 Hz).

(2) [4-[3-[2-(2,4-Dichlorophenyl)-5-isopropyl-4-oxazolyl]-2-methylpropionyl]-2-methylphenoxy] acetic acid The desired compound was obtained in an analogous manner as in (2) of Example 2.

White Amorphous $^1$H-NMR (CDCl$_3$, 400 MHz) δ: 1.18(d, 3H, J=7 Hz), 1.22(d, 3H, J=7 Hz), 1.28(d, 3H, J=7 Hz), 2.28(s, 3H), 2.64(dd, 1H, J=7, 14 Hz), 2.98(dd, 1H, J=7 Hz, 14 Hz), 3.13(m, 1H), 3.95(m, 1H), 4.64(s, 2H), 6.66(d, 1H, J=8 Hz), 7.30(dd, 1H, J=2 Hz, 8 Hz), 7.48(d, 1H, J=2 Hz), 7.76(dd, 1H, J=2 Hz, 8 Hz), 7.81(m, 1H), 7.82(d, 1H, J=8 Hz). IR (KBr) cm$^{-1}$: 3427, 2970, 2931, 2873, 1740, 1672, 1599, 1564, 1502, 1456, 1383, 1271, 1230, 1120.

Example 23

2-[4-[3-[2-(2,4-Dichlorophenyl)-5-isopropyl-4-oxazolyl]-2-methylpropionyl]-2-methylphenoxy]-2-methylpropionic acid (1) Ethyl 2-[4-[3-[2-(2,4-dichlorophenyl)-5-isopropyl-4-oxazolyl]-2-methylpropionyl]-2-methylphenoxy]-2-methylpropionate The desired compound was obtained in an analogous manner as in (2) of Example 1.

$^1$H-NMR (CDCl$_3$, 400 MHz) δ: 1.20(d, 3H, J=7 Hz), 1.22(d, 3H, J=7 Hz), 1.27(d, 3H, J=7 Hz), 1.63(s, 3H), 1.63(s, 3H), 2.23(s, 3H), 2.62(dd, 1H, J=7 Hz, 14 Hz), 2.99(dd, 1H, J=7 Hz, 14 Hz), 3.10(m, 1H), 3.99(m, 1H), 4.20(q, 2H, J=7 Hz), 6.58(d, 1H, J=8 Hz), 7.30(dd, 1H, J=2 Hz, 8 Hz), 7.48(d, 1H, J=2 Hz), 7.73(dd, 1H, J=2 Hz, 8 Hz), 7.80(d, 1H, J=2 Hz), 7.85(d, 1H, J=8 Hz).

(2) 2-[4-[3-[2-(2,4-Dichlorophenyl)-5-isopropyl-4-oxazolyl]-2-methylpropionyl]-2-methylphenoxy]-2-methylpropionic acid The desired compound was obtained in an analogous manner as in (3) of Example 1.

White amorphous $^1$H-NMR (CDCl$_3$, 400 MHz) δ: 1.16(d, 3H, J=7 Hz), 1.21(d, 3H, J=7 Hz), 1.27(d, 3H, J=7 Hz), 1.65(s, 3H), 1.66(s, 3H), 2.23(s, 3H), 2.63(dd, 1H, J=7 Hz, 14 Hz), 2.97(dd, 1H, J=7 Hz, 14 Hz), 3.13(m, 1H), 3.94(m, 1H), 6.71(d, 1H, J=8 Hz), 7.26(m, 1H), 7.46(d, 1H, J=2 Hz), 7.61(dd, 1H, J=2 Hz, 8 Hz), 7.7-7.9(m, 2H). IR (KBr) cm$^{-1}$: 3456, 3431, 2972, 2933, 2873, 1740, 1674, 1599, 1564, 1498, 1462, 1385, 1257, 1142, 1119.

Example 24

[4-[3-[4-Isopropyl-2-(4-trifluoromethyl)phenyl-5-thiazolyl]propenoyl]-2-methylphenoxy]acetic acid (1) 3-[4-Isopropyl-2-(4-trifluoromethylphenyl)thiazol-5-yl]-1-(4-methoxymethoxy-3-methylphenyl) propenone To a mixture of dry MeOH (3 mL) and dry THF (3 mL), 4-isopropyl-2-(4-trifluoromethylphenyl)thiazol-5-carboxyl aldehyde (803 mg, 2.68 mmol), 1-(4-methoxymethoxy3-methylphenyl)ethanone (521 mg, 2.68 mmol) and sodium methoxide (9 mg, 0.13 mmol) were added. The resulting mixture was stirred for 14 hours at room temperature. Sodium methoxide (36 mg, 0.53 mmol) and dry MeOH (3 mL) were added again to the mixture. The resulting mixture was stirred for 26 hours at room temperature. The solvent was removed under reduced pressure. Ethyl acetate (30 mL) was added to the residue. The residue was washed with water (40 mL). The aqueous layer was extracted with ethyl acetate (30 mL, 20 mL). The organic layer was added to the aqueous layer. The mixture was washed with a saturated saline (20 mL), dried over anhydrous sodium sulfate. The solvent was removed under reduced pressure. The residue was purified by column chromatography on silica gel with ethyl acetate/hexane (1/9) to give the desired compound (1.04 g) as a yellow crystal (yield 81%).

$^1$H-NMR (CDCl$_3$, 400 MHz) δ: 1.39(d, 6H, J=7 Hz), 2.33(s, 3H), 3.43(m, 1H), 3.51(s, 3H), 5.30(s, 2H), 7.14(d, 1H, J=8 Hz), 7.30(d, 1H, J=15 Hz), 7.71(d, 2H, J=8 Hz), 7.8-7.9 (m, 2H), 8.04 (d, 1H, J=15 Hz), 8.11 (d, 2H, J=8 Hz)

(2) 1-(4-Hydroxy-3-methylphenyl)-3-[4-isopropyl-2-(4-trifluoromethylphenyl)thiazol-5-yl]propenone In a mixture of isopropanol (4 mL) and THF (16 mL), 3-[4-isopropyl-2-(4-trifluoromethylphenyl)thiazol-5-yl]-1-(4-methoxymethoxy3-methylphenyl)propenone (1.04 g, purity 99.6%, 2.18 mmol) was dissolved. To the mixture, a 1M aqueous solution of hydrochloric acid (2.6 mL) was added. The resulting mixture was stirred for 4 hours at room temperature, and for 19 hours and 30 minutes at 65° C. The solvent was removed under reduced pressure. The residue was suspended in a mixture of ethanol (6 mL) and hexane (2 mL). The crystals were filtered, washed with a mixture of ethanol (2 mL) and hexane (2 mL), and with hexane (2 mL), and dried for 30 minutes at room temperature under reduced pressure to give the desired compound (908 mg) as a yellow crystal (yield 97%).

$^1$H-NMR (CDCl$_3$, 400 MHz) δ: 1.39(d, 6H, J=7 Hz), 2.32(s, 3H), 3.44(m, 1H), 6.85(d, 1H, J=8 Hz), 7.31(d, 1H, J=15 Hz), 7.71(d, 2H, J=8 Hz), 7.81(dd, 1H, J=2 Hz, 8 Hz), 7.81(bs, 1H), 8.03(d, 1H, J=15 Hz), 8.11(d, 2H, J=8 Hz).

(3) Ethyl [4-[3-[4-isopropyl-2-(4-trifluoromethyl) phenyl-5-thiazolyl]propenoyl]-2-methylphenoxy] acetate The desired compound was obtained in an analogous manner as in (1) of Example 2.

$^1$H-NMR (CDCl$_3$, 400 MHz) δ: 1.31(t, 3H, J=7 Hz), 1.39(d, 6H, J=7 Hz), 2.38(s, 3H), 3.44(m, 1H), 4.29(q, 2H, J=7 Hz), 4.74(s, 2H), 6.77(d, 1H, J=8 Hz), 7.29(d, 1H, J=15 Hz), 7.71(d, 2H, J=8 Hz), 7.86(dd, 1H, J=2 Hz, 8 Hz), 7.88(bs, 1H), 8.03(d, 1H, J=15 Hz), 8.11(d, 2H, J=8 Hz).

(4) [4-[3-[4-Isopropyl-2-(4-trifluoromethyl)phenyl-5-thiazolyl]propenoyl]-2-methylphenoxy]acetic acid The desired compound was obtained in an analogous manner as in (2) of Example 2.
Yellow crystal (mp: 203-205° C. (dec.)) $^1$H-NMR (CD$_3$OD/CDCl$_3$=1/20, 400 MHz) δ: 1.39(d, 6H, J=7 Hz), 2.37(s, 3H), 3.44(m, 1H), 4.71(s, 2H), 6.82(d, 1H, J=8 Hz), 7.30(d, 1H, J=15 Hz), 7.72(d, 2H, J=8 Hz), 7.8-7.9(m, 2H), 8.03(d, 1H, J=15 Hz), 8.11(d, 2H, J=8 Hz). IR (KBr) cm$^{-1}$: 2964, 2870, 1761, 1741, 1601, 1581, 1329, 1269, 1230, 1188, 1171, 1132, 1109, 1168, 823.

Example 25

2-[4-[3-[4-Isopropyl-2-(4-trifluoromethyl)phenyl-5-thiazolyl]propenoyl]-2-methylphenoxy]-2-methylpropionic acid (1) Ethyl 2-[4-[3-[4-isopropyl-2-(4-trifluoromethyl)phenyl-5-thiazole]propenoyl]-2-methylphenoxy]-2-methylpropionate The desired compound was obtained in an analogous manner as in (2) of Example 1.
$^1$H-NMR (CDCl$_3$, 400 MHz) δ: 1.23(t, 3H, J=7 Hz), 1.38(d, 6H, J=7 Hz), 1.68(s, 6H), 2.32(s, 3H), 3.44(m, 1H), 4.24(q, 2H, J=7 Hz), 6.68(d, 1H, J=8 Hz), 7.29(d, 1H, J=15 Hz), 7.71(d, 2H, J=8 Hz), 7.78(dd, 1H, J=2 Hz, 8 Hz), 7.87(d, 1H, J=2 Hz), 8.02(d, 1H, J=15 Hz), 8.11(d, 2H, J=8 Hz).

(2) 2-[4-[3-[4-Isopropyl-2-(4-trifluoromethyl)phenyl-5-thiazole]propenoyl]-2-methylphenoxy]-2-methylpropionic acid The desired compound was obtained in an analogous manner as in (3) of Example 1.
Yellow crystal (mp: 187-189° C.) $^1$H-NMR (CDCl$_3$, 400 MHz) δ: 1.38(d, 6H, J=7 Hz), 1.72(s, 6H), 2.33(s, 3H), 3.46(m, 1H), 6.82(d, 1H, J=8 Hz), 7.28(d, 1H, J=15 Hz), 7.71(d, 2H, J=8 Hz), 7.82(dd, 1H, J=2 Hz, 8 Hz), 7.88(d, 1H, J=2 Hz), 8.04(d, 1H, J=15 Hz), 8.10(d, 2H, J=8 Hz). IR (KBr) cm$^{-1}$: 3466, 2972, 1740, 1657, 1655, 1639, 1603, 1500, 1327, 1325, 1273, 1169, 1128, 1068.

Example 26

[4-[3-[4-Isopropyl-2-(4-methoxyphenyl)-5-thiazolyl]propionyl]-2-methylphenoxy]propionic acid (1) Ethyl [4-[3-[4-isopropyl-2-(4-methoxyphenyl)-5-thiazolyl]propionyl]-2-methylphenoxy]propionate The desired compound was obtained in an analogous manner as in (2) of Example 1.
$^1$H-NMR (CDCl$_3$, 400 MHz) δ: 1.29(t, 3H, J=7 Hz), 1.32(d, 6H, J=7 Hz), 2.32(s, 3H), 3.11(dq, 1H, J=7 Hz, 7 Hz), 3.1-3.3(m, 4H), 3.84(s, 3H), 4.27(q, 2H, J=7 Hz), 4.70(s, 2H), 6.71(d, 1H, J=8 Hz), 6.8-7.0(m, 2H), 7.7-7.9(m, 4H).

(2) [4-[3-[4-Isopropyl-2-(4-methoxyphenyl)-5-thiazolyl]propionyl]-2-methylphenoxy]propionic acid The desired compound was obtained in an analogous manner as in (3) of Example 1.
Pale yellow crystal (mp: 170-172° C.) $^1$H-NMR (CDCl$_3$, 400 MHz) δ: 1.31(d, 6H, J=7 Hz), 2.32(3H, s), 3.11(dq, 1H, J=7 Hz, 7 Hz), 3.1-3.3(m, 4H), 3.84(s, 3H), 4.76(s, 2H), 6.74(d, 1H, J=8 Hz), 6.91(d, 2H, J=9 Hz), 7.7-7.9(m, 4H). IR (KBr) cm$^{-1}$: 2970, 1726, 1672, 1605, 1517, 1456, 1367, 1304, 1302, 1300, 1282, 1261, 1209, 1176, 1130, 1065, 1034, 1018, 995, 843, 824.

Example 27

[4-[3-[2-(3,5-Difluorophenyl)-4-isopropylthiazol-5-yl]propionyl]-2-methylphenoxy]acetic acid (1) Ethyl [4-[3-[2-(3,5-difluorophenyl)-4-isopropylthiazol-5-yl]propionyl]-2-methylphenoxy]acetate The desired compound was obtained in an analogous manner as in (1) of Example 2.
$^1$H-NMR (CDCl$_3$, 400 MHz) δ: 1.28(t, 3H, J=7 Hz), 1.32(d, 6H, J=7 Hz), 2.33(s, 3H), 3.14(m, 1H), 3.2-3.3(m, 4H), 4.27(q, 2H, J=7 Hz), 4.71(s, 2H), 6.71(d, 1H, J=8 Hz), 6.7-6.9(m, 1H), 7.4-7.5(m, 2H), 7.7-7.8(m, 2H).

(2) [4-[3-[2-(3,5-Difluorophenyl)-4-isopropylthiazol-5-yl]propionyl]-2-methylphenoxy]acetic acid The desired compound was obtained in an analogous manner as in (2) of Example 2.
Pale yellow crystal (mp: 125-128° C.) $^1$H-NMR (CDCl$_3$, 400 MHz) δ: 1.31(d, 6H, J=7 Hz), 2.32(s, 3H), 3.13(m, 1H), 3.2-3.3(m, 4H), 4.75(s, 2H), 6.7-6.8(m, 2H), 7.4-7.5(m, 2H), 7.7-7.9(m, 2H). IR (KBr) cm$^{-1}$: 3446, 2970, 2929, 2376, 1749, 1743, 1676, 1620, 1599, 1533, 1504, 1502, 1458, 1439, 1363, 1321, 1271, 1230, 1176, 1136, 1134, 1132, 1072, 1053, 987, 879, 847, 808, 677.

Example 28

2-[4-[3-[2-(3,5-Difluorophenyl)-4-isopropyl-5-thiazolyl]propionyl]-2-methylphenoxy]-2-methylpropionic acid (1) Ethyl 2-[4-[3-[2-(3,5-difluorophenyl)-4-isopropyl-5-thiazolyl]propionyl]-2-methylphenoxy]-2-methylpropionate The desired compound was obtained in an analogous manner as in (2) of Example 1.
$^1$H-NMR (CDCl$_3$, 400 MHz) δ: 1.21(t, 3H, J=7 Hz), 1.31(d, 6H, J=7 Hz), 1.65(s, 6H), 2.27(3H, s), 3.13(dq, 1H, J=7 Hz, 7 Hz), 3.2-3.3(m, 4H), 4.22(q, 2H, J=7 Hz), 6.62(d, 1H, J=9 Hz), 6.79(dt, 1H, J=2 Hz, 9 Hz), 7.4-7.5(m, 2H), 7.69(dd, 1H, J=2 Hz, 9 Hz), 7.79(d, 1H, J=2 Hz).

(2) 2-[4-[3-[2-(3,5-Difluorophenyl)-4-isopropylthiazol-5-yl]propionyl]-2-methylphenoxy]-2-methylpropionic acid The desired compound was obtained in an analogous manner as in (3) of Example 1.
White crystal (mp: 132-133° C.) $^1$H-NMR (CDCl$_3$, 400 MHz) δ: 1.31(d, 6H, J=7 Hz), 1.69(s, 6H), 2.28(s, 3H), 3.13(dq, 1H, J=7 Hz, 7 Hz), 3.2-3.3(m, 4H), 6.77(d, 1H, J=9 Hz), 6.7-6.8(m, 1H), 7.4-7.5(m, 2H), 7.73(dd, 1H, J=2 Hz, 9 Hz), 7.81(d, 1H, J=2 Hz). IR (KBr) cm$^{-1}$: 2974, 2927, 1741, 1652, 1620, 1605, 1535, 1506, 1502, 1458, 1363, 1327, 1321, 1284, 1263, 1147, 1122, 1068, 987, 876, 850, 675.

Example 29

[4-[3-[4-Isopropyl-2-(2-naphthyl)-5-thiazolyl]propionyl]-2-methylphenoxy]acetic acid (1) Ethyl [4-[3-[4-isopropyl-2-(2-naphthyl)-5-thiazolyl]propionyl]-2-methylphenoxy]acetate The desired compound was obtained in an analogous manner as in (1) of Example 2.

$^1$H-NMR (CDCl$_3$, 400 MHz) δ: 1.28(3H, t, J=7 Hz), 1.37(6H, d, J=7 Hz), 2.33(3H, s), 3.18(1H, m), 3.2-3.3(4H, m), 4.25(2H, q, J=7 Hz), 4.69(2H, s), 6.71(1H, d, J=8 Hz), 6.4-6.5(2H, m), 7.7-7.9(5H, m), 8.04(1H, dd, J=2 Hz, 8 Hz), 8.34(1H, s)

(2) [4-[3-[4-Isopropyl-2-(2-naphthyl)-5-thiazolyl]propionyl]-2-methylphenoxy]acetic acid The desired compound was obtained in an analogous manner as in (2) of Example 2.

Pale yellow crystal (mp: 97-100° C.) $^1$H-NMR (CDCl$_3$, 400 MHz) δ: 1.37(6H, d, J=7 Hz), 2.32(3H, s), 3.18(1H, m), 3.2-3.3(4H, m), 4.76(2H, s), 6.74(1H, d, J=8 Hz), 7.4-7.5 (2H, m), 7.7-7.9(5H, m), 8.03(1H, dd, J=2 Hz, 8 Hz), 8.33(1H, s). IR (KBr) cm$^{-1}$: 3845, 3745, 3429, 2962, 2929, 2368, 2345, 1749, 1676, 1601, 1506, 1502, 1362, 1255, 1228, 1132, 1068, 858, 813, 748, 476, 420

Example 30

2-[4-[3-[4-Isopropyl-2-(2-naphthyl)-5-thiazolyl]propionyl]-2-methylphenoxy]-2-methylpropionic acid The desired compound was obtained in an analogous manner as in (3) of Example 1.

White crystal (mp: 164-166° C.) $^1$H-NMR (CDCl$_3$, 400 MHz) δ: 1.36(d, 6H, J=7 Hz), 1.68(s, 6H), 2.28(s, 3H), 3.16(dq, 1H, J=7 Hz, 7 Hz), 3.2-3.4(m, 4H), 6.76(d, 1H, J=8 Hz), 7.4-7.5(m, 2H), 7.73(dd, 1H, J=2 Hz, 8 Hz), 7.8-7.9(m, 3H), 7.82(d, 1H, J=2 Hz), 8.03(dd, 1H, J=2 Hz, 9 Hz), 8.34(s, 1H). IR (KBr) cm$^{-1}$: 2966, 1741, 1655, 1620, 1605, 1365, 1284, 1263, 1180, 1147, 1146, 808, 750.

Example 31

[4-[3-[2-(4-Butylphenyl)-4-isopropyl-5-thiazolyl]propionyl]-2-methylphenoxy]acetic acid (1) Ethyl [4-[3-[2-(4-butylphenyl)-4-isopropyl-5-thiazolyl]propionyl]-2-methylphenoxy]acetate The desired compound was obtained in an analogous manner as in (1) of Example 2.

$^1$H-NMR (CDCl$_3$, 400 MHz) δ: 0.92(3H, t, J=7 Hz), 1.29(3H, t, J=7 Hz), 1.32(6H, d, J=7 Hz), 1.3-1.4(2H, m), 1.5-1.6(2H, m), 2.32(3H, s), 2.62(2H, t, J=8 Hz), 3.15(1H, m), 3.2-3.3(4H, m), 4.26(2H, q, J=7 Hz), 4.70(2H, s), 6.71(1H, d, J=8 Hz), 7.19(2H, d, J=8 Hz), 7.7-7.8(4H, m).

(2) [4-[3-[2-(4-Butylphenyl)-4-isopropyl-5-thiazolyl]propionyl]-2-methylphenoxy]acetic acid The desired compound was obtained in an analogous manner as in (2) of Example 2.

Pale yellow amorphous $^1$H-NMR (CDCl$_3$, 400 MHz) δ: 0.92(3H, t, J=7 Hz), 1.31(6H, d, J=7 Hz), 1.3-1.4(2H, m), 1.5-1.7(2H, m), 2.31 (3H, s), 2.62(2H, t, J=8 Hz), 3.12(1H, m), 3.1-3.3(4H, m), 4.74(2H, s), 6.72(1H, d, J=8 Hz), 7.19(2H, d, J=8 Hz), 7.7-7.8(4H, m). IR (KBr) cm$^{-1}$: 3435, 2960, 2929, 2870, 2860, 2368, 1741, 1676, 1601, 1502, 1456, 1414, 1360, 1319, 1275, 1230, 1176, 1138, 1065, 985, 885, 837, 812, 627.

Example 32

2-[4-[3-[2-(4-Butylphenyl)-4-isopropyl-5-thiazolyl]propionyl]-2-methylphenoxy]-2-methylpropionic acid (1) Ethyl 2-[4-[3-[2-(4-butylphenyl)-4-isopropyl-5-thiazolyl]propionyl]-2-methylphenoxy]-2-methylpropionate The desired compound was obtained in an analogous manner as in (2) of Example 1.

$^1$H-NMR (CDCl$_3$, 400 MHz) δ: 0.92(t, 3H, J=7 Hz), 1.21(t, 3H, J=7 Hz), 1.32(d, 6H, J=7 Hz), 1.3-1.4(m, 2H), 1.5-1.7(m, 2H), 1.65(s, 6H), 2.26(s, 3H), 2.62(t, 2H, J=8 Hz), 3.11(dq, 1H, J=7 Hz, 7 Hz) 3.2-3.3(m, 4H), 4.22(q, 2H, J=7 Hz), 6.61(d, 1H, J=9 Hz), 7.19(d, 2H, J=8 Hz), 7.70(dd, 1H, J=2 Hz, 9 Hz), 7.79(d, 2H, J=8 Hz), 7.79(d, 1H, J=2 Hz).

(2) 2-[4-[3-[2-(4-Butylphenyl)-4-isopropyl-5-thiazolyl]propionyl]-2-methylphenoxy]-2-methylpropionic acid The desired compound was obtained in an analogous manner as in (3) of Example 1.

White crystal (mp: 121-122° C.) $^1$H-NMR (CDCl$_3$, 400 MHz) d: 0.92(t, 3H, J=7 Hz), 1.31(d, 6H, J=7 Hz), 1.3-1.4 (m, 2H), 1.5-1.7(m, 2H), 1.68(s, 6H), 2.27(s, 3H), 2.62(t, 2H, J=8 Hz), 3.11(dq, 1H, J=7 Hz, 7 Hz), 3.2-3.3(m, 4H), 6.76(1d, 1H, J=9 Hz), 7.19(d, 2H, J=8 Hz), 7.72(dd, 1H, J=2 Hz, 9 Hz), 7.78(d, 2H, J=8 Hz), 7.80(d, 1H, J=2 Hz).

Example 33

[4-[3-[4-Isopropyl-2-(4-trifluoromethyl)phenyl-5-thiazolyl]propionyl]-2-chlorophenoxy]acetic acid (1) Ethyl [4-[3-[4-isopropyl-2-(4-trifluoromethyl)phenyl-5-thiazolyl]propionyl]-2-chlorophenoxy]acetate The desired compound was obtained in an analogous manner as in (1) of Example 2.

$^1$H NMR (CDCl$_3$, 400 MHz) δ: 1.29(t, 3H, J=7 Hz), 1.34(d, 6H, J=7 Hz), 3.15(m, 1H), 3.26(s, 4H), 4.27(q, 2H, J=7 Hz), 4.77(s, 2H), 6.85(d, 1H, J=9 Hz), 7.64(d, 2H, J=8 Hz), 7.84(dd, 1H, J=2 Hz, 9 Hz), 8.00(d, 2H, J=8 Hz), 8.03(d, 1H, J=2 Hz).

(2) [4-[3-[4-Isopropyl-2-(4-trifluoromethyl)phenyl-5-thiazolyl]propionyl]-2-chlorophenoxy]acetic acid The desired compound was obtained in an analogous manner as in (2) of Example 2.

White crystal (mp: 149-151° C.) $^1$H-NMR (CDCl$_3$, 400 MHz) δ: 1.34(d, 6H, J=7 Hz), 3.15(m, 1H), 3.26(s, 4H), 4.82(s, 2H), 6.90(d, 1H, J=8 Hz), 7.64(d, 2H, J=8 Hz), 7.87(dd, 1H, J=2 Hz, 8 Hz), 8.00(d, 2H, J=8 Hz), 8.04(d, 1H, J=2 Hz). IR (KBr) cm$^{-1}$: 1724, 1684, 1616, 1595, 1496, 1406, 1360, 1329, 1281, 1232, 1203, 1157, 1117, 1016, 839, 773.

Example 34

[4-[3-[2-(4-Trifluoromethyl)phenyl-4-isopropyl-5-thiazolyl]propionyl]-2-chlorophenoxy]-2-methylpropionic acid (1) Ethyl [4-[3-[2-(4-trifluoromethyl)phenyl-4-isopropyl-5-thiazolyl]propionyl]-2-chlorophenoxy]-2-methylpropionate The desired compound was obtained in an analogous manner as in (2) of Example 1.
$^1$H-NMR (CDCl$_3$, 400 MHz) δ: 1.23(t, 3H, J=7 Hz), 1.33(d, 6H, J=7 Hz), 1.68(s, 6H), 3.14(m, 1H), 3.25(s, 4H), 4.23(q, 2H, J=7 Hz), 6.82(d, 1H, J=8 Hz), 7.64(d, 2H, J=8 Hz), 7.75(dd, 1H, J=2 Hz, 8 Hz), 8.00(d, 2H, J=8 Hz), 8.01(d, 1H, J=2 Hz).

(2) [4-[3-[2-(4-Trifluoromethyl)phenyl-4-isopropyl-5-thiazolyl]propionyl]-2-chlorophenoxy]-2-methylpropionic acid The desired compound was obtained in an analogous manner as in (3) of Example 1.
Pale yellow amorphous
$^1$H-NMR (CDCl$_3$, 400 MHz) δ: 1.33(d, 6H, J=7 Hz), 1.71(s, 6H), 3.14(m, 1H), 3.26(s, 4H), 7.02(d, 1H, J=8 Hz), 7.64(d, 2H, J=8 Hz), 7.80(dd, 1H, J=2 Hz, 8 Hz), 8.00(d, 2H, J=8 Hz), 8.03(d, 1H, J=2 Hz)

Example 35

[4-[3-[2-(2,4-Dichlorophenyl)-5-isopropyl-4-oxazolyl]propionyl]-2-chlorophenoxy]acetic acid (1) Ethyl [4-[3-[2-(2,4-dichlorophenyl)-5-isopropyl-4-oxazolyl]propionyl]-2-chlorophenoxy]acetate The desired compound was obtained in an analogous manner as in (1) of Example 3.
$^1$H-NMR (CDCl$_3$, 400 MHz) δ: 1.28(t, 3H, J=7 Hz), 1.30(d, 6H, J=7 Hz), 2.96(t, 2H, J=7 Hz), 3.17(m, 1H), 3.33(t, 2H, J=7 Hz), 4.27(q, 2H, J=7 Hz), 4.76(s, 2H), 6.83(d, 1H, J=8 Hz), 7.30(dd, 1H, J=2 Hz, 8 Hz), 7.49(d, 1H, J=2 Hz), 7.8-7.9(m, 2H), 8.05(d, 1H, J=8 Hz).

(2) [4-[3-[2-(2,4-Dichlorophenyl)-5-isopropyl-4-oxazolyl]propionyl]-2-chlorophenoxy]acetic acid The desired compound was obtained in an analogous manner as in (2) of Example 2.
White crystal (mp: 134-137° C.) $^1$H-NMR (CDCl$_3$, 400 MHz) δ: 1.31(d, 6H, J=7 Hz), 2.96(t, 2H, J=7 Hz), 3.19(m, 1H), 3.30(t, 2H, J=7 Hz), 4.78(s, 2H), 6.84(d, 1H, J=8 Hz), 7.31(dd, 1H, J=2 Hz, 8 Hz), 7.49(d, 1H, J=2 Hz), 7.81(dd, 1H, J=2 Hz, 8 Hz), 7.84(d, 1H, J=8 Hz), 8.03(d, 1H, J=2 Hz). IR (KBr) cm$^{-1}$: 3437, 1720, 1687, 1593, 1562, 1497, 1458, 1406, 1221, 1203, 1088, 1038, 833, 808, 744, 692.

Example 36

2-[4-[3-[2-(2,4-Dichlorophenyl)-5-isopropyl-4-oxazolyl]propionyl]-2-chlorophenoxy]-2-methylpropionic acid (1) Ethyl 2-[4-[3-[2-(2,4-dichlorophenyl)-5-isopropyl-4-oxazolyl]propionyl]-2-chlorophenoxy]-2-methylpropionate The desired compound was obtained in an analogous manner as in (2) of Example 1.
$^1$H-NMR (CDCl$_3$, 400 MHz) δ: 1.23(t, 3H, J=7 Hz), 1.30(d, 6H, J=7 Hz), 1.67(s, 6H), 2.95(t, 2H, J=7 Hz), 3.17(m, 1H), 3.31(t, 2H, J=7 Hz), 4.23(q, 2H, J=7 Hz), 6.80(d, 1H, J=9 Hz), 7.30(dd, 1H, J=2 Hz, 9 Hz), 7.49(d, 1H, J=2 Hz), 7.77(dd, 1H, J=2 Hz, 9 Hz), 7.88(d, 1H, J=9 Hz), 8.03(d, 1H, J=2 Hz).

(2) 2-[4-[3-[2-(2,4-Dichlorophenyl)-5-isopropyl-4-oxazolyl]propionyl]-2-chlorophenoxy]-2-methylpropionic acid The desired compound was obtained in an analogous manner as in (2) of Example 1.
White crystal (mp: 76-79° C.) $^1$H-NMR (CDCl$_3$, 400 MHz) δ: 1.30(d, 6H, J=7 Hz), 1.68(s, 6H), 2.95(t, 2H, J=7 Hz), 319(m, 1H), 3.29(t, 2H, J=7 Hz), 6.97(d, 1H, J=9 Hz), 7.29(dd, 1H, J=2 Hz, 9 Hz), 7.48(d, 1H, J=2 Hz), 7.72(dd, 1H, J=2 Hz, 8 Hz), 7.84(d, 1H, J=8 Hz), 8.02(d, 1H, J=2 Hz). IR (KBr) cm$^{-1}$: 2968, 1720, 1686, 1593, 1562, 1493, 1460, 1402, 1385, 1306, 1259, 1200, 1180, 1146, 1059, 968, 902, 879, 822, 777, 739, 700, 571.

Example 37

[4-[3-[5-Isopropyl-2-(4-trifluoromethyl)phenyl-4-thiazolyl]propionyl]-2-methylphenoxy]acetic acid (1) [4-[3-[5-Isopropyl-2-(4-trifluoromethyl)phenyl-4-thiazolyl]propionyl]-2-methylphenoxy]ethyl acetate The desired compound was obtained in an analogous manner as in (1) of Example 2.
$^1$H-NMR (CDCl$_3$, 400 MHz) δ: 1.29(t, 3H, J=7 Hz), 1.33(d, 6H, J=7 Hz), 2.31(s, 3H), 3.14(t, 2H, J=7 Hz), 3.37(m, 1H), 3.43(t, 2H, J=7 Hz), 4.26(q, 2H, J=7 Hz), 4.70(s, 2H), 6.70(d, 1H, J=9 Hz), 7.63(d, 2H, J=8 Hz), 7.8-7.9(m, 2H), 7.95(d, 2H, J=8 Hz).

(2) [4-[3-[2-(4-Trifluoromethyl)phenyl-5-isopropyl-4-thiazolyl]propionyl]-2-methylphenoxy]acetic acid The desired compound was obtained in an analogous manner as in (1) of Example 2.
White crystal (mp: 125-132° C.) $^1$H-NMR (CDCl$_3$, 400 MHz) δ: 1.33(d, 6H, J=7 Hz), 2.30(s, 3H), 3.14(t, 2H, J=7 Hz), 3.37(m, 1H), 3.42(t, 2H, J=7 Hz), 4.74(s, 2H), 6.73(d, 1H, J=9 Hz), 7.63(d, 2H, J=8 Hz), 7.8-7.9(m, 2H), 7.94(d, 2H, J=8 Hz). IR (KBr) cm$^{-1}$: 3425, 2964, 1751, 1686, 1603, 1581, 1504, 1433, 1410, 1365, 1329, 1252, 1173, 1132, 1111, 1068, 1018, 989, 841, 815, 675, 611.

Example 38

2-[4-[3-[5-Isopropyl-2-(4-trifluoromethyl)phenyl-4-thiazolyl]propionyl]-2-methylphenoxy]-2-methylpropionic acid (1) Ethyl [4-[3-[5-isopropyl-2-(4-trifluoromethyl)phenyl-4-thiazolyl]propionyl]-2-methylphenoxy]-2-methylpropionate The desired compound was obtained in an analogous manner as in (2) of Example 1.
$^1$H-NMR (CDCl$_3$, 400 MHz) δ: 1.21(t, 3H, J=7 Hz), 1.33(d, 6H, J=7 Hz), 1.64(s, 6H), 2.25(s, 3H), 3.14(t, 2H, J=7 Hz), 3.36(m, 1H), 3.41(t, 2H, J=7 Hz), 4.21(q, 2H, J=7 Hz), 6.61(d, 1H, J=8 Hz), 7.63(d, 2H, J=8 Hz), 7.74(dd, 1H, J=2, 8 Hz), 7.81(bs, 1H), 7.95(d, 2H, J=8 Hz).

(2) 2-[4-[3-[5-Isopropyl-2-(4-trifluoromethyl)phenyl-4-thiazolyl]propionyl]-2-methylphenoxy]-2-methylpropionic acid The desired compound was obtained in an analogous manner as in (3) of Example 1.
White crystal (mp: 89-93° C.) $^1$H-NMR (CDCl$_3$, 400 MHz) δ: 1.34(d, 6H, J=7 Hz), 1.67(s, 6H), 2.25(s, 3H), 3.14(t, 2H, J=7 Hz), 3.38(m, 1H), 3.40(t, 2H, J=7 Hz), 6.75(d, 1H, J=8 Hz), 7.63(d, 2H, J=8 Hz), 7.72(dd, 1H, J=2 Hz, 8 Hz), 7.82(d, 1H, J=2 Hz), 7.93(d, 2H, J=8 Hz). IR (KBr) cm$^{-1}$: 2964, 1720, 1678, 1601, 1498, 1458, 1410, 1365, 1325, 1257, 1169, 1135, 1068, 1016, 972, 847, 771, 606.

Example 39

[4-[3-[2-(2,4-Dichlorophenyl)-5-isopropyl-4-thiazolyl]propionyl]-2-methylphenoxy]acetic acid (1) [4-[3-[2-(2,4-Dichlorophenyl)-5-isopropyl-4-thiazolyl]propionyl]-2-methylphenoxy]acetic acid The desired compound was obtained in an analogous manner as in (2) of Example 2.
White crystal (mp: 158-161° C.) $^1$H-NMR (CDCl$_3$, 400 MHz) δ: 1.34(d, 6H, J=7 Hz), 2.29(s, 3H), 3.15(t, 2H, J=7 Hz), 3.37(m, 1H), 3.40(t, 2H, J=7 Hz), 4.73(s, 2H), 6.71(d, 1H, J=8 Hz), 7.2-7.3(m, 1H), 7.47(d, 1H, J=2 Hz), 7.7-7.9 (m, 2H), 8.03(d, 1H, J=8 Hz). IR (KBr) cm$^{-1}$: 2953, 1740, 1664, 1602, 1583, 1551, 1504, 1475, 1429, 1363, 1317, 1277, 1254, 1244, 1176.1132, 1103, 1063, 989, 887, 862, 821, 777, 683.

Example 40

2-[4-[3-[2-(2,4-Dichlorophenyl)-5-isopropyl-4-thiazolyl]propionyl]-2-methylphenoxy]-2-methylpropionic acid (1) Ethyl 2-[4-[3-[2-(2,4-dichlorophenyl)-5-isopropyl-4-thiazolyl]propionyl]-2-methylphenoxy]-2-methylpropionate The desired compound was obtained in an analogous manner as in (2) of Example 1.
$^1$H-NMR (CDCl$_3$, 400 MHz) δ: 1.21(t, 3H, J=7 Hz), 1.34(d, 6H, J=7 Hz), 1.62(s, 6H), 2.25(s, 3H), 3.14(t, 2H, J=7 Hz), 3.36(m, 1H), 3.40(t, 2H, J=7 Hz), 4.22(q, 2H, J=7 Hz), 6.60(d, 1H, J=9 Hz), 7.27(dd, 1H, J=2, 9 Hz), 7.47(d, 1H, J=2 Hz), 7.73(dd, 1H, J=2 Hz, 8 Hz), 7.81(bs, 1H), 8.07(d, 1H, J=8 Hz).

(2) 2-[4-[3-[2-(2,4-Dichlorophenyl)-5-isopropyl-4-thiazolyl]propionyl]-2-methylphenoxy]-2-methylpropionic acid The desired compound was obtained in an analogous manner as in (2) of Example 1.
White amorphous
$^1$H-NMR (CDCl$_3$, 400 MHz) δ: 1.34(d, 6H, J=7 Hz), 1.66(s, 6H), 2.25(s, 3H), 3.14(t, 2H, J=7 Hz), 3.38(m, 1H), 3.39(t, 2H, J=7 Hz), 6.73(d, 1H, J=8 Hz), 7.26(dd, 1H, J=2 Hz, 9 Hz), 7.46(d, 1H, J=2 Hz), 7.70(dd, 1H, J=2 Hz, 8 Hz), 7.81(d, 1H, J=2 Hz), 8.02(d, 1H, J=8 Hz).

Example 41

[5-[3-[4-Isopropyl-2-(4-trifluoromethyl)phenyl-5-thiazolyl]propionyl]-2-methylphenoxy]acetic acid (1) Ethyl [5-[3-[4-isopropyl-2-(4-trifluoromethyl)phenyl-5-thiazolyl]propionyl]-2-methylphenoxy]acetate The desired compound was obtained in an analogous manner as in (1) of Example 2.
$^1$H-NMR (CDCl$_3$, 400 MHz) δ: 1.30(t, 3H, J=7 Hz), 1.33(d, 6H, J=7 Hz), 2.35(s, 3H), 3.14(m, 1H), 3.2-3.3(m, 4H), 4.26(q, 2H, J=7 Hz), 4.71(s, 2H), 7.24(d, 1H, J=7 Hz), 7.35(d, 1H, J=2 Hz), 7.49(dd, 1H, J=2 Hz, 7 Hz), 7.64(d, 2H, J=8 Hz), 8.00(d, 2H, J=8 Hz).

(2) [5-[3-[4-Isopropyl-2-(4-trifluoromethyl)phenyl-5-thiazolyl]propionyl]-2-methylphenoxy]acetic acid The desired compound was obtained in an analogous manner as in (2) of Example 2.
Pale yellow crystal (mp: 130-133° C.) $^1$H-NMR (DMSO-d$_6$, 400 MHz) δ: 1.28(d, 6H, J=7 Hz), 2.26(s, 3H), 3.1-3.3 (m, 3H), 3.38(t, 2H, J=7 Hz), 4.77(s, 2H), 7.30(d, 1H, J=8 Hz), 7.35(s, 1H), 7.55(d, 1H, J=8 Hz), 7.81(d, 2H, J=8 Hz), 8.05(d, 2H, J=8 Hz). IR (KBr) cm$^{-1}$: 2968, 2931, 2872, 1767, 1741, 1678, 1618, 1616, 1579, 1533, 1506, 1450, 1412, 1362, 1327, 1294, 1242, 1167, 1126, 1124, 1122, 1068, 1016, 978, 874, 847, 777, 609.

Example 42

2-[5-[3-[4-Isopropyl-2-(4-trifluoromethyl)phenyl-5-thiazolyl]propionyl]-2-methylphenoxy]-2-methylpropionic acid (1) Ethyl 2-[5-[3-[4-isopropyl-2-(4-trifluoromethylphenyl)-5-thiazolyl]propionyl]-2-methylphenoxy]-2-methylpropionate The desired compound was obtained in an analogous manner as in (2) of Example 1.
$^1$H-NMR (CDCl$_3$, 400 MHz) δ: 1.26(t, 3H, J=7 Hz), 1.33(d, 6H, J=7 Hz), 1.63(s, 6H), 2.29(s, 3H), 3.14(m, 1H), 3.2-3.4(m, 4H), 4.26(q, 2H, J=7 Hz), 7.22(d, 1H, J=8 Hz), 7.31(d, 1H, J=2 Hz), 7.47(dd, 1H, J=2 Hz, 8 Hz), 7.64(d, 2H, J=8 Hz), 8.00(d, 2H, J=8 Hz)

(2) 2-[5-[3-[4-Isopropyl-2-(4-trifluoromethylphenyl)-5-thiazolyl]propionyl]-2-methylphenoxy]-2-methylpropionic acid The desired compound was obtained in an analogous manner as in (3) of Example 1.

White crystal (mp: 124-126° C.) $^1$H-NMR (DMSO-$d_6$, 400 MHz) δ: 1.27(d, 6H, J=7 Hz), 1.54(s, 6H), 2.22(s, 3H), 3.1-3.4(m, 5H), 7.30(s, 1H), 7.31(d, 1H, J=8 Hz), 7.56(d, 1H, J=8 Hz), 7.81(d, 2H, J=8 Hz), 8.05(d, 2H, J=8 Hz), 13.12(bs, 1H) IR (KBr) cm$^{-1}$: 2972, 1736, 1684, 1618, 1616, 1498, 1452, 1412, 1327, 1259, 1167, 1130, 1068, 1016, 972, 845, 777.

Example 43

2-[4-[3-[4-Isopropyl-2-(4-trifluoromethyl)phenyl-5-thiazolyl]propionyl]-2-methylphenoxy]propionic acid

(1) Ethyl 2-[4-[3-[4-isopropyl-2-(4-trifluoromethyl)phenyl-5-thiazolyl]propionyl]-2-methylphenoxy]propionate Intermediate of Example 3, namely 3-[2-(4-trifluoromethyl)phenyl-4-isopropyl-5-thiazolyl]-1-(3-methyl-4-hydroxyphenyl)propan-1-one (433 mg, 1.00 mmol) and potassium carbonate (166 mg, 1.20 mmol) was suspended in acetone (10 mL). To the suspension, ethyl 2-bromopropionate (216 mg, 1.20 mmol) was added while cooling with ice. The mixture was stirred for 20 hours at room temperature. The reaction mixture was poured into ice water, and extracted with ethyl acetate. The organic layer was washed with water (20 mL) and a saturated saline (20 mL), dried over anhydrous sodium sulfate. The solvent was removed under reduced pressure. The residue was purified by column chromatography on silica gel with hexane/ethyl acetate (5/1) to give the desired compound (534 mg) as a colorless oil (quantitative yield).

$^1$H NMR (CDCl$_3$, 400 MHz) δ: 1.24(t, 3H, J=7 Hz), 1.33(d, 6H, J=7 Hz), 1.66(d, 3H, J=7 Hz), 2.31(s, 3H), 3.15(dq, 1H, J=7 Hz, 7 Hz), 3.2-3.3(m, 4H), 4.20(q, 2H, J=7 Hz), 4.82(q, 1H, J=7 Hz), 6.68(d, 1H, J=8 Hz), 7.64(d, 2H, J=8 Hz), 7.76(dd, 1H, J=2 Hz, 8 Hz), 7.80(d, 1H, J=2 Hz), 8.00(d, 2H, J=8 Hz).

(2) 2-[4-[3-[4-Isopropyl-2-(4-trifluoromethyl)phenyl-5-thiazolyl]propionyl]-2-methylphenoxy]propionic acid The desired compound was obtained in an analogous manner as in (2) of Example 2.

White crystal (mp: 120-123° C.) $^1$H-NMR (CDCl$_3$, 400 MHz) δ: 1.33(d, 6H, J=7 Hz), 1.70(d, 3H, J=7 Hz), 2.31(s, 3H), 3.15(dq, 1H, J=7 Hz, 7 Hz), 3.2-3.3(m, 4H), 4.88(q, 1H, J=7 Hz), 6.73(d, 1H, J=9 Hz), 7.63(d, 2H, J=8 Hz), 7.77(dd, 1H, J=2, 9 Hz), 7.80(d, 1H, J=2 Hz), 7.99(d, 2H, J=8 Hz). IR (KBr) cm$^{-1}$: 2950, 1740, 1670, 1600, 1500, 1450, 1320, 1300, 1275, 1250, 1190, 1160, 1130, 1060, 845.

Example 44

4-[3-[4-Methyl-2-(4-trifluoromethyl)phenyl-5-thiazolyl]propionyl]-2-methylphenoxy]acetic acid

(1) Ethyl [4-[3-[4-methyl-2-(4-trifluoromethyl)phenyl-5-thiazolyl]propionyl]-2-methylphenoxy]acetate The desired compound was obtained in an analogous manner as in (1) of Example 2.

$^1$H-NMR (CDCl$_3$, 400 MHz) δ: 1.29(t, 3H, J=7 Hz), 2.31(s, 3H), 2.46(s, 3H), 3.2-3.3(m, 4H), 4.26(q, 2H, J=7 Hz), 4.70(s, 2H), 6.71(d, 1H, J=8 Hz), 7.64(d, 2H, J=8 Hz), 7.76(dd, 1H, J=2 Hz, 8 Hz), 7.80(d, 1H, J=2 Hz), 7.97(d, 2H, J=8 Hz).

(2) [4-[3-[4-Methyl-2-(4-trifluoromethyl)phenyl-5-thiazolyl]propionyl]-2-methylphenoxy]acetic acid The desired compound was obtained in an analogous manner as in (1) of Example 2.

White crystal (mp: 194-195° C.) $^1$H-NMR (CDCl$_3$, 400 MHz) δ: 2.32(s, 3H), 2.45(s, 3H), 3.2-3.3(m, 4H), 4.75(s, 2H), 6.74(d, 1H, J=8 Hz), 7.64(d, 2H, J=8 Hz), 7.7-7.9(m, 2H), 7.96(d, 2H, J=8 Hz). IR (KBr) cm$^{-1}$: 3500, 2900, 1780, 1730, 1680, 1610, 1500, 1410, 1370, 1330, 1240, 1180, 1080, 850.

Example 45

2-[4-[3-[4-Hexyl-2-(4-trifluoromethyl)phenyl-5-thiazolyl]-1-propenyl]-2-methylphenoxy]-2-methylpropionic acid

(1) Ethyl 2-[4-[3-[4-hexyl-2-(4-trifluoromethyl)phenyl-5-thiazolyl]-1-propenyl]-2-methylphenoxy]-2-methylpropionate The desired compound was obtained in an analogous manner as in (2) of Example 1.

$^1$H-NMR (CDCl$_3$, 400 MHz) δ: 0.88(t, 3H, J=7 Hz), 1.25(t, 3H, J=7 Hz), 1.3-1.5(m, 6H), 1.58(s, 6H), 1.7-1.8(m, 2H), 2.22(s, 3H), 2.74(t, 2H, J=7 Hz), 3.65(d, 2H, J=6 Hz), 4.24(q, 2H, J=7 Hz), 6.16(dt, 1H, J=6 Hz, 16 Hz), 6.40(d, 1H, J=16 Hz), 6.60(d, 1H, J=8 Hz), 7.04(dd, 1H, J=2, 8 Hz), 7.16(d, 1H, J=2 Hz), 7.64(d, 2H, J=8 Hz), 7.99(d, 2H, J=8 Hz)

(2) 2-[4-[3-[4-Hexyl-2-(4-trifluoromethyl)phenyl-5-thiazolyl]-1-propenyl]-2-methylphenoxy]-2-methylpropionic acid The desired compound was obtained in an analogous manner as in (3) of Example 1.

Pale brown powder (mp: 152-155° C.) $^1$H-NMR (CDCl$_3$, 400 MHz) δ: 0.88(t, 3H, J=7 Hz), 1.2-1.5(m, 6H), 1.61(s, 6H), 1.7-1.8(m, 2H), 2.23(s, 3H), 2.74(t, 2H, J=7 Hz), 3.66(d, 2H, J=6 Hz), 6.20(dt, 1H, J=6 Hz, 16 Hz), 6.41(d, 1H, J=16 Hz), 6.78(d, 1H, J=8 Hz), 7.09(dd, 1H, J=2 Hz, 8 Hz), 7.19(d, 1H, J=2 Hz), 7.64(d, 2H, J=8 Hz), 7.99(d, 2H, J=8 Hz). IR (KBr) cm$^{-1}$: 2920, 1700, 1610, 1500, 1445, 1320, 1250, 1160, 1120, 1060, 900, 840.

Example 46

2-[5-[3-[4-Hexyl-2-(4-trifluoromethyl)phenyl-5-thiazolyl]propionyl]-2-methylphenoxy]-2-methyl-propionic acid (1) Ethyl 2-[5-[3-[4-hexyl-2-(4-trifluoromethyl)phenyl-5-thiazolyl]propionyl]-2-methylphenoxy]-2-methylpropionate The desired compound was obtained in an analogous manner as in (2) of Example 1.

$^1$H-NMR (CDCl$_3$, 400 MHz) δ: 0.89(t, 3H, J=7 Hz), 1.26(t, 3H, J=7 Hz), 1.3-1.4(m, 6H), 1.54(s, 6H), 1.7-1.8(m, 2H), 2.29(s, 3H), 2.74(t, 2H, J=8 Hz), 3.2-3.3(m, 4H), 4.26(q, 2H, J=7 Hz), 7.22(d, 1H, J=8 Hz), 7.31(d, 2H, J=8 Hz), 7.47(dd, 1H, J=2 Hz, 8 Hz), 7.64(d, 1H, J=2 Hz), 7.98(d, 2H, J=8 Hz).

(2) 2-[5-[3-[4-Hexyl-2-(4-trifluoromethyl)phenyl-5-thiazolyl]propionyl]-2-methylphenoxy]-2-methyl-propionic acid The desired compound was obtained in an analogous manner as in (3) of Example 1.

Yellow oil $^1$H-NMR (CDCl$_3$, 400 MHz) δ: 0.88(t, 3H, J=7 Hz), 1.2-1.4(m, 6H), 1.64(s, 6H), 1.7-1.8(m, 2H), 2.29(s, 3H), 2.73(t, 2H, J=7 Hz), 3.2-3.3(m, 4H), 7.25(d, 1H, J=8 Hz), 7.43(s, 1H), 7.50(d, 1H, J=8 Hz), 7.62(d, 2H, J=8 Hz), 7.96(d, 2H, J=8 Hz)

Example 47

[4-[3-[4-Ethyl-2-(4-trifluoromethyl)phenyl-5-thiazolyl]propionyl]-2-methylphenoxy]acetic acid (1) Ethyl [4-[3-[4-ethyl-2-(4-trifluoromethyl)phenyl-5-thiazolyl]propionyl]-2-methylphenoxy]acetate The desired compound was obtained in an analogous manner as in (1) of Example 2.

$^1$H-NMR (CDCl$_3$, 400 MHz) δ: 1.30(t, 3H, J=7 Hz), 1.32(t, 3H, J=7 Hz), 2.33(s, 3H), 2.79(q, 2H, J=7 Hz), 3.2-3.3(m, 4H), 4.27(q, 2H, J=7 Hz), 4.71(s, 2H), 6.71(d, 1H, J=8 Hz), 7.64(d, 2H, J=8 Hz), 7.8-7.9(m, 2H), 7.99(d, 2H, J=8 Hz).

(2) [4-[3-[4-Ethyl-2-(4-trifluoromethyl)phenyl-5-thiazolyl]propionyl]-2-methylphenoxy]acetic acid The desired compound was obtained in an analogous manner as in (2) of Example 2.

White crystal (mp: 165-167° C.) $^1$H-NMR (CDCl$_3$, 400 MHz) δ: 1.31(t, 3H, J=7 Hz), 2.32(s, 3H), 2.79(q, 2H, J=7 Hz), 3.2-3.3(m, 4H), 4.76(s, 2H), 6.74(d, 1H, J=8 Hz), 7.64(d, 2H, J=8 Hz), 7.80(dd, 1H, J=2, 8 Hz), 7.81(d, 1H, J=2 Hz), 7.97(d, 2H, J=8 Hz). IR (KBr) cm$^{-1}$: 2975, 1760, 1740, 1670, 1610, 1600, 1580, 1500, 1440, 1360, 1320, 1260, 1220, 1160, 1130, 1110, 1960, 840, 820.

Example 48

2-[4-[3-[4-Ethyl-2-(4-trifluoromethyl)phenyl-5-thiazolyl]propionyl]-2-methylphenoxy]-2-methylpropionic acid (1) Ethyl 2-[4-[3-[4-ethyl-2-(4-trifluoromethyl)phenyl-5-thiazolyl]propionyl]-2-methylphenoxy]-2-methylpropionate The desired compound was obtained in an analogous manner as in (2) of Example 1.

$^1$H-NMR (CDCl$_3$, 400 MHz) δ: 1.21(t, 3H, J=7 Hz), 1.32(t, 3H, J=7 Hz), 1.55(s, 6H), 2.27(s, 3H), 2.79(q, 2H, J=7 Hz), 3.2-3.3(m, 4H), 4.22(q, 2H, J=7 Hz), 6.62(d, 1H, J=8 Hz), 7.64(d, 2H, J=8 Hz), 7.69(dd, 1H, J=2, 8 Hz), 7.79(d, 1H, J=2 Hz), 7.99(d, 2H, J=8 Hz).

(2) 2-[4-[3-[4-Ethyl-2-(4-trifluoromethyl)phenyl-5-thiazolyl]propionyl]-2-methylphenoxy]-2-methyl-propionic acid The desired compound was obtained in an analogous manner as in (3) of Example 1.

White crystal (mp: 168-170° C.) $^1$H-NMR (CDCl$_3$, 400 MHz) δ: 1.31(t, 3H, J=7 Hz), 1.69(s, 6H), 2.27(s, 3H), 2.78(q, 2H, J=7 Hz), 3.2-3.3(m, 4H), 6.75(d, 1H, J=8 Hz), 7.63(d, 2H, J=8 Hz), 7.72(dd, 1H, J=2, 8 Hz), 7.80(d, 1H, J=2 Hz), 7.97(d, 2H, J=8 Hz). IR (KBr) cm$^{-1}$: 2950, 1720, 1680, 1660, 1580, 1540, 1440, 1400, 1360, 1320, 1260, 1160, 1120, 1060, 960, 840, 820.

Example 49

[4-[3-[4-Isopropyl-2-(4-methylphenyl)-5-thiazolyl]propionyl]-2-methylphenoxy]acetic acid (1) Ethyl [4-[3-[4-isopropyl-2-(4-methylphenyl)-5-thiazolyl]propionyl]-2-methylphenoxy]acetate The desired compound was obtained in an analogous manner as in (1) of Example 2.

$^1$H-NMR (CDCl$_3$, 400 MHz) δ: 1.29(t, 3H, J=7 Hz), 1.31(d, 6H, J=7 Hz), 2.32(s, 3H), 2.37(s, 3H), 3.12(dq, 1H, J=7 Hz, 7 Hz), 3.2-3.3(m, 4H), 4.27(q, 2H, J=7 Hz), 4.70(s, 2H), 6.71(d, 1H, J=8 Hz), 7.19(d, 2H, J=8 Hz), 7.7-7.8(m, 4H).

(2) [4-[3-[4-Isopropyl-2-(4-methylphenyl)-5-thiazolyl]propionyl]-2-methylphenoxy]acetic acid The desired compound was obtained in an analogous manner as in (2) of Example 2.

White crystal (mp: 188-190° C.) $^1$H-NMR (CDCl$_3$, 400 MHz) δ: 1.32(d, 6H, J=7 Hz), 2.32(s, 3H), 2.37(s, 3H), 3.12(dq, 1H, J=7 Hz, 7 Hz), 3.2-3.3(m, 4H), 4.75(s, 2H), 6.73(d, 1H, J=8 Hz), 7.18(d, 2H, J=8 Hz), 7.7-7.8(m, 4H). IR (KBr) cm$^{-1}$: 2950, 1720, 1670, 1600, 1580, 1500, 1440, 1360, 1310, 1280, 1210, 1180, 1120, 1060, 820.

Example 50

2-[4-[3-[4-Isopropyl-2-(4-methylphenyl)-5-thiazolyl]propionyl]-2-methylphenoxy]-2-methylpropionic acid

(1) Ethyl 2-[4-[3-[4-isopropyl-2-(4-methylphenyl)-5-thiazolyl]propionyl]-2-methylphenoxy]-2-methylpropionate The desired compound was obtained in an analogous manner as in (2) of Example 1.

$^1$H-NMR (CDCl$_3$, 400 MHz) δ: 1.21(t, 3H, J=7 Hz), 1.32(d, 6H, J=7 Hz), 1.65(s, 6H), 2.26(s, 3H), 2.37(s, 3H), 3.11(dq, 1H, J=7 Hz, 7 Hz), 3.2-3.3(m, 4H), 4.22(q, 2H, J=7 Hz), 6.61(d, 1H, J=8 Hz), 7.19(d, 2H, J=8 Hz), 7.69(dd, 1H, J=2, 8 Hz), 7.7-7.8(m, 3H).

(2) 2-[4-[3-[4-Isopropyl-2-(4-methylphenyl)-5-thiazolyl]propionyl]-2-methylphenoxy]-2-methylpropionic acid The desired compound was obtained in an analogous manner as in (3) of Example 1.

Yellow amorphous $^1$H-NMR (CDCl$_3$, 400 MHz) δ: 1.31(d, 6H, J=7 Hz), 1.67(s, 6H), 2.27(s, 3H), 2.36(s, 3H), 3.11(dq, 1H, J=7 Hz, 7 Hz), 3.2-3.3(m, 4H), 6.72(d, 1H, J=8 Hz), 7.18(d, 2H, J=8 Hz), 7.70(d, 1H, J=8 Hz), 7.72(d, 2H, J=8 Hz), 7.79(s, 1H).

Example 51

(Pharmacological Experimetnt 1)

I. Method (1) Measurement of PPARα, γ, δ Transactivation Activity

PPARα, γ, δ transactivation activity of each compound [Examples 1-8 and known PPARδ agonist (L-16504: Berger, J., et al. (1999), J. Biol. Chem., 274:6718-6725)] was measured in the manner described below.

1) Material

CV-1 cells were obtained from Tohoku University Aging Medical Laboratory, Medical Cell Collection Center. All test compounds were dissolved in dimethylsulfoxide (DMSO). Final concentration of DMSO was 0.1%.

2) Plasmid

Receptor expression plasmid (GAL4-hPPARα LBD GAL4-hPPARγ LBD, GAL4-hPPARδ LBD), Reporter plasmid (UASx4-TK-LUC), and β-galactosidase expression plasmid (βGAL) similar to Kliewer, S. A., et al., ((1992) Nature, 358:771-774) were used.

3) Transfection

CV-1 cells were seeded in 24 well culture plates at 2×10$^5$ cells per well, and cultured for 24 hours OPTI-MEM I Reduced Serum Medium (Life Technologies, 500 µL/well) containing 4%-fetal bovine serum (FBS). After washing with OPTI-MEM, transfection mixture (250 µL/well) containing 0.03 µg of GAL4-hPPARδ LBD, 0.25 µg of UASx4-TK-LUC, 0.35 µg of βGAL, and 2 µL of lipofection reagent, DMRIE-C (Life Technologies) were added. The cells were incubated for 5 hours at 37° C.

4) Cell Treatment by Addition of Test Compound

The cells were washed and incubated for 40 hours in the presence of the test compound (final concentration was $10^{-7}$M or $10^{-6}$M).

5) Measurement of the Level of Reporter Gene Expression

The culture medium was removed and the cells were washed with PBS twice. A solubilizing buffer (100 µL/well) containing 25 mM Tris-PO$_4$ (pH 7.8), 15% v/v glycerol, 2% CHAPS, 1% Lecithin, 1% BSA, 4 mM EGTA (pH 8.0), 8 mM MgCl$_2$, 1 mM DTT was added. After the incubation for 10 minutes at room temperature, a portion (20 µL) of the solution was transferred into a 96-well plate. Subsequently, 100 µL of luciferase substrate solution (Piccagene: available from Nippon Gene Co., Ltd.) was added, and a luminous intensity per one second (luciferase activity) was measured using a microluminoreader (Type MLR-100, Corona Electrics Co., Ltd.). Each luciferase activety was corrected by the transfection efficiency which was calculated from β-galactosidase activity. The assay method of β-galactosidase activity was as follows: A portion (50 µL) of the solubilized sample was transferred into another 96-well plate; 100 µL of ONPG (2-nitrophenyl-β-galactopyranoside) solution was added and incubated for 5 minutes at room temperature. 50 µL of a reaction stopping solution (1M sodium carbonate solution) was added. Then the absorbance at 414 nm was measured.

A relative PPAR activity was calculated as follows: 0% (luciferase activity of cells treated with DMSO (0.1%) alone), 100% (luciferase activity of cells treated with a control (PPARα: $10^{-4}$ M WY-165041, PPARγ: $10^{-5}$ M Rosiglitazone, PPARδ: $10^{-4}$ M L-165041)

II. Results

The results are shown in Table 8.

TABLE 8

|  | α | γ | δ |
|---|---|---|---|
| Example 1 | 76 | 10 | 84 |
| Example 2 | 0 | 2 | 61 |
| Example 3 | 0 | 5 | 101 |
| Example 4 | 11 | 12 | 86 |
| Example 5 | 1 | 6 | 75 |
| Example 6 | 0 | 6 | 73 |
| Example 7 | 0 | 3 | 61 |
| Example 8 | 0 | 4 | 48 |
| GW-2433 | 64 | 7 | 52 |
| GW-501516 | 0 | 1 | 90 |

Relative activities for PPAR transactivation were shown. Each value represents as % of control. Cells were cultured in the presence of compounds at $10^{-7}$ M except Example 1 ($10^{-6}$ M).

positive control:
α: $10^{-4}$ M WY-14643
γ: $10^{-5}$ M Rosiglitazone
δ: $10^{-4}$ M L-165041

It is clear that the compounds of Examples have PPARδ transactivation activity similar to or more potent than L-165041.

Example 52

(Pharmacological Tests 2)

PPAR transactivation activities of the compounds of Examples 9-50 were assayed in the same manner as described in Example 51. The results are shown in Table 9.

TABLE 9

| Test compound | α | γ | δ |
|---|---|---|---|
| Example 9 | (0) | (4) | (84) |
| Example 10 | 0 | 1 | 67 |
| Example 11 | 0 | 1 | 56 |
| Example 12 | 75 | 31 | 45 |
| Example 13 | 63 | 17 | 62 |
| Example 14 | 0 | 0 | 42 |
| Example 15 | (NT) | (NT) | (58) |
| Example 16 | 62 | 3 | 57 |
| Example 17 | NT | NT | (90) |
| Example 18 | 0 | 1 | 70 |
| Example 19 | 0 | 2 | 86 |
| Example 20 | NT | NT | (72) |
| Example 21 | NT | NT | (62) |
| Example 22 | 0 | 0 | 52 |
| Example 23 | NT | NT | (93) |
| Example 24 | 0 | 0 | 75 |
| Example 25 | NT | NT | 61 |
| Example 26 | NT | NT | 18 |
| Example 27 | NT | NT | 37 |
| Example 28 | 0 | NT | 21 |
| Example 29 | NT | NT | 27 |
| Example 30 | (85) | (47) | (76) |
| Example 31 | NT | NT | 51 |
| Example 32 | 1 | NT | 14 |
| Example 33 | 0 | 1 | 44 |
| Example 34 | 5 | 3 | 66 |
| Example 35 | (0) | (1) | (71) |
| Example 36 | (14) | (5) | (92) |
| Example 37 | NT | NT | (71) |
| Example 38 | (3) | (9) | (69) |
| Example 39 | NT | NT | (65) |
| Example 40 | (22) | (3) | (72) |
| Example 41 | (5) | (60) | NT |
| Example 42 | (68) | (55) | NT |
| Example 43 | 3 | 5 | 42 |
| Example 44 | (0) | (0) | (38) |
| Example 45 | 90 | 20 | 49 |
| Example 46 | (78) | (69) | (46) |
| Example 47 | 0 | 0 | 57 |
| Example 48 | (84) | (13) | (51) |
| Example 49 | 0 | 2 | 56 |
| Example 50 | 104 | 50 | 30 |

Relative activities for PPAR transactivation were shown.

Each value represents as % of control. Cells were cultured in the presence of compounds at $10^{-7}$ M except the compounds that the values are given in parentheses (for example, Example 44 etc.). Those compounds were assayed at $10^{-6}$ M.

NT or (NT) means "not tested".

positive control:

α: $10^{-4}$ M WY-14643

γ: $10^{-5}$ M Rosiglitazone

δ: $10^{-4}$ M L-165041

It is clear from Table 9 that the compounds of Examples 9-50 have potent PPARδ transactivation activities. It is also clear from Tables 8 & 9 that the compound of the formula (I) wherein $R^2$ is methyl (Example 44) is inferior in the PPARδ transactivation activity to the other compounds of the formula (I)-wherein $R^2$ is ethyl (Example 47 etc.), isopropyl (Example 3 etc.), or hexyl (Example 11 etc.). Therefore, the alkyl group of $R^2$ preferably has two or more carbon atoms.

Example 53

(Pharmacological Experiment 2)

HDL Cholesterol Elevating Effect

I. Method

HDL cholesterol elevating effect was measured by using db/db mice, which are hereditary obesity mice. The db/db mice (10 weeks old) were divided into groups based on serum HDL cholesterol levels. Each of the compounds of the present invention (compounds synthesized in Examples 4 and 10) and GW-501516 was orally administered for one week twice daily. Mice of the control group (to which no agent was administered) were orally given 1% methyl cellulose solution. After 16 hours from the final administration, blood sample was collected, and serum HDL cholesterol level was measured. HDL cholesterol was separated by electrophoresis on agarose gels (Chol/Trig Combo, Helena Laboratories). Serum total cholesterol levels were measured enzymaticallly using a kit (Pure Auto, Daiichi Chemicals) by an automatic analyzer (7060E type, Hitachi Ltd.). HDL cholesterol levels were calculated from total cholesterol levels and HDL cholesterol/total cholesterol ratios.

II. Results

Serum HDL cholesterol levels of experiments groups are shown in Table 10. Each value represents as % of the control group.

TABLE 10

| Test compound | Dose (mg/kg/b.i.d.) | Ratio of increasing HDL cholesterol (% to control) |
|---|---|---|
| Example 4 | 10 | 176 |
| Example 10 | 10 | 134 |
| GW-501516 | 10 | 149 |

As shown in Table 10, compounds of the present invention raised serum HDL cholesterol significantly. It is clear that they have potent HDL cholesterol elevating effect.

Therefore, the compounds of the invention are useful for the treatment of dyslipidemia.

The invention claimed is:

1. A compound having the following formula (I):

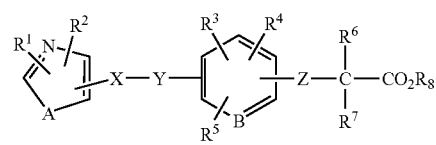

or a salt thereof, wherein:

$R^1$ is phenyl or naphthyl, each of which can have substituents selected from the group consisting of $C_{1-8}$ alkyl, $C_{1-8}$ alkyl having halogen, $C_{1-8}$ alkoxy, $C_{1-8}$ alkoxy having halogen, $C_{2-8}$ alkenyl, $C_{2-8}$ alkynyl, halogen, $C_{2-7}$ acyl, benzoyl, hydroxyl, nitro, amino, phenyl and pyridyl;

$R^2$ is $C_{2-8}$ alkyl;

A is oxygen or sulfur;

X is a $C_{1-8}$ alkylene chain which can have a $C_{1-8}$ alkyl substituent and which can contain a double bond;

Y is C(=O), CH=CH, or C(=CH$_2$);

each of $R^3$, $R^4$ and $R^5$ is hydrogen, $C_{1-8}$ alkyl, $C_{1-8}$ alkyl having halogen, $C_{1-8}$ alkoxy, $C_{1-8}$ alkoxy having halogen, $C_{2-8}$ alkenyl, $C_{2-8}$ alkynyl, halogen, $C_{2-7}$ acyl, benzoyl, hydroxyl, nitro, amino, phenyl, or pyridyl;

B is CH;

Z is oxygen or sulfur;

each of $R^6$ and $R^7$ is hydrogen or $C_{1-8}$ alkyl; and $R^8$ is hydrogen or $C_{1-8}$ alkyl.

2. The compound or a salt thereof defined in claim 1, wherein X is a $C_{1-8}$ alkylene chain.

3. The compound or a salt thereof defined in claim 1, wherein $R^1$ is attached to the $2^{nd}$ position.

4. The compound or a salt thereof defined in any one of claims 1 to 3, wherein $R^8$ is hydrogen.

5. The compound or a salt thereof defined in any one of claims 1 to 4, wherein the substituents of $R^3$, $R^4$ and $R^5$ other than hydrogens are placed at ortho-positions with respect to -Z-$CR^6R^7CO_2R^8$.

* * * * *

UNITED STATES PATENT AND TRADEMARK OFFICE
CERTIFICATE OF CORRECTION

| | | |
|---|---|---|
| PATENT NO. | : 7,265,137 B2 | Page 1 of 1 |
| APPLICATION NO. | : 10/486783 | |
| DATED | : September 4, 2007 | |
| INVENTOR(S) | : Sakuma et al. | |

It is certified that error appears in the above-identified patent and that said Letters Patent is hereby corrected as shown below:

On the Title Page,

After Item (*) Notice

Should read,

The Term of this Patent Subsequent to Patent Number 6,787,552 has been disclaimed Signed and Sealed this Fifth Day of May, 2009

JOHN DOLL
*Acting Director of the United States Patent and Trademark Office*